US012565609B2

(12) United States Patent
Khramov et al.

(10) Patent No.: US 12,565,609 B2
(45) Date of Patent: Mar. 3, 2026

(54) WELLBORE FLUIDS INCLUDING EMULSIFIERS, AND RELATED METHODS

(71) Applicant: Schlumberger Technology Corporation, Sugar Land, TX (US)

(72) Inventors: Dimitri Khramov, Katy, TX (US); Evgeny Barmatov, Cambridge (GB)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 18/800,795

(22) Filed: Aug. 12, 2024

(65) Prior Publication Data

US 2026/0042949 A1 Feb. 12, 2026

(51) Int. Cl.

| | |
|---|---|
| ***C09K 8/36*** | (2006.01) |
| ***C07C 309/15*** | (2006.01) |
| ***C07D 233/26*** | (2006.01) |
| ***E21B 21/00*** | (2006.01) |

(52) U.S. Cl.

CPC .............. *C09K 8/36* (2013.01); *C07C 309/15* (2013.01); *C07D 233/26* (2013.01); *E21B 21/00* (2013.01)

(58) Field of Classification Search

CPC ... C09K 8/02; C09K 8/03; C09K 8/32; C09K 8/34; C09K 8/035; C09K 8/36; E21B 21/00; C07C 309/15; C07D 233/26

See application file for complete search history.

(56) References Cited

U.S. PATENT DOCUMENTS

| | | | | |
|---|---|---|---|---|
| 3,259,572 A * | 7/1966 | Dickson | C07C 255/00 516/27 |
| 3,738,996 A * | 6/1973 | Bloch et al. | C07D 233/14 548/352.1 |
| 4,859,245 A * | 8/1989 | Schilling | C08L 95/005 106/284.4 |
| 11,827,838 B2 * | 11/2023 | Khramov | C09K 23/16 |
| 2006/0025321 A1 * | 2/2006 | Treybig | C09K 8/68 510/382 |
| 2017/0283680 A1 * | 10/2017 | Chen | C09K 8/36 |
| 2021/0380873 A1 * | 12/2021 | Kalgaonkar | C09K 8/68 |

FOREIGN PATENT DOCUMENTS

| | | | |
|---|---|---|---|
| WO | WO-2016065270 A1 * | 4/2016 | C08K 5/3445 |
| WO | 2022066205 A1 | 3/2022 | |

OTHER PUBLICATIONS

Khramov et al., Targeted improvements in chemistry of common fluid additives increase temperature stability of non-aqueous drilling fluids, AADE-22-FTCE-054, 2022, 7 pages.

* cited by examiner

*Primary Examiner* — Angela M DiTrani Leff
(74) *Attorney, Agent, or Firm* — Jeffrey D. Frantz

(57) ABSTRACT

A wellbore fluid includes an oleaginous base fluid, and an emulsifier including a reaction product of an amide and a sultone. The amide may include a bis-amide, an imidazoline-amide, or a mixture including the bis-amide and the imidazoline-amide. The bis-amide may include a reaction product of one or more fatty acids and one or more sultones. The imidazoline-amide may include a condensation product of the bis-amide. Related methods of forming the emulsifier and using the emulsifier in a wellbore fluid while drilling an earth formation are also disclosed.

11 Claims, 9 Drawing Sheets

WELLBORE FLUIDS INCLUDING EMULSIFIERS, AND RELATED METHODS

CROSS REFERENCE TO RELATED APPLICATIONS

N/A.

BACKGROUND

Wellbore drilling operations include drilling a borehole into an earth formation to access reservoirs of hydrocarbons and other subsurface resources. One or more casings may subsequently be cemented in the borehole to form a wellbore. During drilling of the borehole and/or wellbore, various fluids may be circulated into the borehole and/or wellbore through a drill pipe and drill bit, and may subsequently flow upward to the surface. For example, a drilling fluid (e.g., an aqueous-based fluid or an oil-based fluid) may be pumped down the inside of the drill pipe, through the drill bit, and into the wellbore. The drilling fluid returns to the surface through the annulus. The drilling fluid may lubricate and cool the drill bit, facilitate transport of formation cuttings to the surface, prevent blowouts by maintaining a hydrostatic pressure greater than the formation pressure, maintain well stability, and reduce fluid loss to the formation.

Drilling fluids may be water-based (aqueous-based), or drilling fluids may be non-aqueous based, such as oil-based or synthetic-based drilling fluids. In non-aqueous drilling fluids, water is the dispersed phase and oil (or a synthetic material) is the dispersion medium, or continuous phase. Non-aqueous drilling fluids may reduce formation damage to water-sensitive formations, such as water-sensitive clays. In addition, non-aqueous drilling fluids may also provide shale stability to the formation.

Non-aqueous drilling fluids may be stabilized with an emulsifier. However, some emulsifiers may negatively impact the rheology of the drilling fluid, such as by increasing the low shear rate viscosity (LSRV) of the drilling fluid, which increases the effective circulating density (ECD) and may result in wellbore integrity issues. Further, some emulsifiers may cause the drilling fluid to exhibit a high gel strength, which may lead to increased surge pressure when mud pumps are restarted after a period of static conditions, resulting in difficulties with inserting or removing the drill string from the well after the well has been in a static condition.

Commercially available emulsifiers include amidoamines and imidazolines. However, imidazolines may not be stable at the high pH of some drilling fluids. For example, exposure to high pH and water may open the imidazoline structure, causing the imidazoline to open to a straight chain. Other problems with imidazolines and amidoamines include the difficulty in manufacturing the imidazolines and amidoamines, which are energy intensive and time-consuming processes. In addition, commercially available emulsifiers are often contaminated with undesired reaction by-products that form during the formation of the emulsifiers. However, the reaction by-products may negatively affect the fluid performance of the drilling fluid and, therefore, require expensive purification processes before use in a drilling fluid.

BRIEF SUMMARY

In some embodiments, a wellbore fluid includes an oleaginous base fluid, and an emulsifier including a reaction product of an amide and a sultone.

In some embodiments, a method of forming an emulsifier for a wellbore fluid includes reacting a polyalkylamine with a fatty acid to form at least one of a bis-amide or an imidazoline-amide, and reacting the at least one of the bis-amide or the imidazoline-amide with a sultone to form an emulsifier.

In some embodiments, a method of drilling a borehole includes drilling a borehole in an earth formation using a drilling fluid and circulating the drilling fluid through the borehole. The drilling fluid includes an oleaginous base fluid and an emulsifier including a reaction product of an amide and a sultone.

This summary is provided to introduce a selection of concepts that are further described below in the detailed description. This summary is not intended to identify key or essential features of the claimed subject matter, nor is it intended to be used as an aid in limiting the scope of the claimed subject matter.

Additional features and advantages of embodiments of the disclosure will be set forth in the description which follows, and in part will be obvious from the description, or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF DRAWINGS

In order to describe the manner in which the above-recited and other features of the disclosure can be obtained, a more particular description will be rendered by reference to specific implementations thereof which are illustrated in the appended drawings. For better understanding, the like elements have been designated by like reference numbers throughout the various accompanying figures. While some of the drawings may be schematic or exaggerated representations of concepts, at least some of the drawings may be drawn to scale. Understanding that the drawings depict some example implementations, the implementations will be described and explained with additional specificity and detail through the use of the accompanying drawings in which.

DETAILED DESCRIPTION

Figure 1:
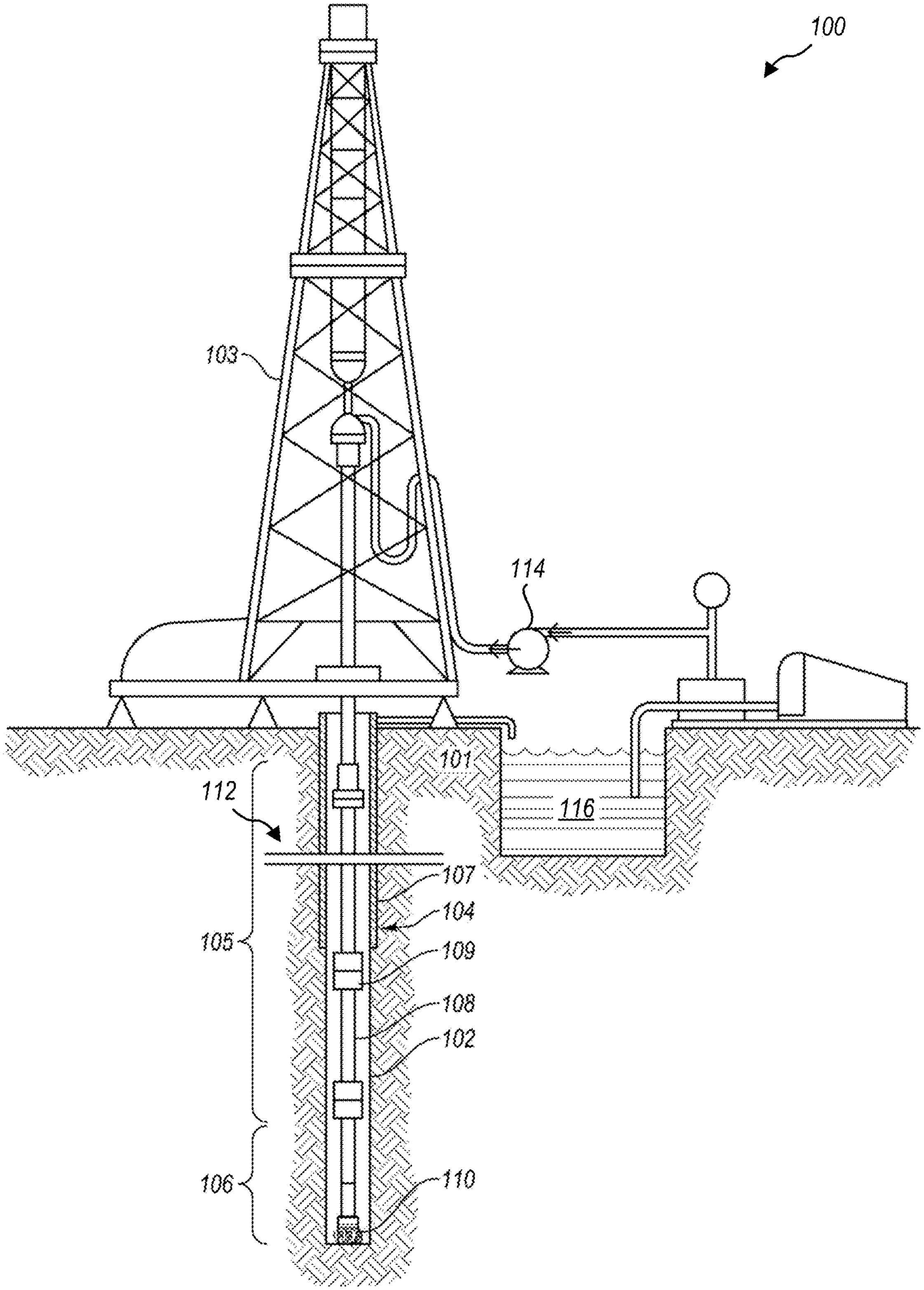
FIG. 1 is a representation of a drilling system for drilling an earth formation to form a wellbore, according to at least one embodiment of the present disclosure.

As used herein, the term "barrel" is a volume equivalent to 42 gallons. Quantities of various materials (e.g., additives) are often quantified in barrels in the oil and gas industry.

As used herein, a "hydrocarbyl" group means and includes a $C_1$ to $C_{100}$ hydrocarbon (e.g., a radical) and may be linear, branched, and/or cyclic (e.g., include one or more cyclic groups, which may be aromatic or non-aromatic). The $C_1$ to $C_{100}$ hydrocarbyl group may be saturated or unsaturated (e.g., include one or more carbon-carbon double bonds (e.g., include one or more alkenyl groups)). Non-limiting examples of hydrocarbyl groups include methyl, ethyl, n-propyl, isopropyl, n-butyl, isobutyl, sec-butyl, tert-butyl, pentyl, iso-amyl, hexyl, heptyl, octyl, cyclopropyl, cyclobutyl, cyclopentyl, cyclohexyl, cyclooctyl, and the like, including substituted analogues. For example, at least one hydrogen atom may be substituted with at least one heteroatom or a heteroatom-containing group, such as a halogen (e.g., F, Cl, Br, I), or at least one functional group, such as $NR'_2$, $OR'$, $SeR'$, $TeR'$, $PR'_2$, $ASR'_2$, $SbR'_2$, $SR'$, $BR'_2$, $SiR'_3$, $GeR'_3$, $SnR'_3$, $PbR'_3$, and the like, wherein R' is hydrogen, alkyl, hydroxyalkyl, carboxyalkyl, or another group, or where at least one heteroatom has been inserted within a hydrocarbyl ring.

As used herein, a fatty acid has a chemical formula of R—COOH, wherein R corresponds to a hydrocarbyl group.

As used herein, the term "bis-amide" refers to a compound having two identical amide groups. A polyamide may include a compound having two or more amide groups, which may or may not be identical.

As used herein, the term "polyalkylamine" refers to a compound having alternating amine and alkyl groups. The polyalkylamine may be linear or branched.

As used herein, a "sulfonic acid" or a "sulfonic acid group" refers to a functional group including a sulfur atom doubly bonded to two oxygen atoms, a hydroxyl group, and a carbon atom of any hybridization. The sulfur atoms of the sulfonic acid group includes two sulfur to oxygen double bonds (S═O), the sulfur single bonded to a hydroxyl group (e.g., in the S—OH), and the sulfur atom single bonded to the carbon atom.

This disclosure generally relates to devices, systems, and methods of manufacturing and using wellbore fluid additives for downhole applications, such as wellbore fluid emulsification using one or more emulsifiers. The emulsifier may be used in a wellbore fluid, such as a drilling fluid, drill-in fluids (also referred to as "reservoir drill-in fluids" (RDF)), workover fluids, spacer fluids (e.g., a fluid introduced into the wellbore after a drilling fluid and prior to a cement composition to flush residual drilling fluid from the annulus), stimulation fluids, or other wellbore fluids. The emulsifier may be used during drilling of a wellbore or borehole for producing hydrocarbons, for storing hydrocarbons, or for forming other types of wellbores and is not limited to the particular type of wellbore being drilled.

The emulsifier may be provided as a component of the wellbore fluid, such as of a drilling fluid. In some embodiments, the emulsifier is used in an oil-based or a synthetic-based wellbore fluid (e.g., an oil-based drilling fluid or a synthetic-based drilling fluid, which may also be referred to as a non-aqueous drilling fluid or an invert emulsion drilling fluid). In some embodiments, the emulsifier is provided to the wellbore fluid as an emulsifier composition including the emulsifier and a carrier fluid (e.g., a base oil).

The emulsifier may include a reaction product of an amide and a sultone. The amide may include a bis-amide, an imidazoline-amide, or a mixture including the bis-amide and the imidazoline-amide. The sultone may include, for example, 1,3-propane sultone and/or 1,4-butane sultone. The emulsifier may include a tertiary amine that is bonded to one or two amide groups and bonded to a sulfonic acid group. In some embodiments, the emulsifier includes a tertiary amine bonded to a terminal amide group, a terminal imidazoline group, and a sulfonic acid group. In some embodiments, the emulsifier includes a tertiary amine bonded to two terminal amide groups and a sulfonic acid group or a sulfonate group. The amide may include a bis-amide comprising a reaction product of one or more polyalkylamines and one or more fatty acids. In some embodiments, the amide includes a condensation product of the bis-amide and includes an imidazoline-amide.

Forming the emulsifier from the sultone may facilitate forming the emulsifier without forming undesired reaction by-products that form during the formation of other types of emulsifiers, such as amidoamine emulsifiers and/or improved syntheses of the emulsifier. For example, the sultone may not substantially react with water. Accordingly, the emulsifier may be formed in the presence of water, which negatively affects the formation of amidoamine emulsifiers. In addition, emulsifiers formed by the bis-amide or by the imidazoline-amide may exhibit relatively similar properties and form stable emulsions in wellbore fluids. By way of comparison, when forming emulsifiers formed by reacting an amide with a dicarboxylic anhydride, the amide must be controlled to comprise a bis-amide while the amount of the imidazoline-amide is reduced since the imidazoline-amide negatively affects the performance of emulsifiers formed by reacting the imidazoline-amide with a dicarboxylic anhydride.

FIG. 1 shows one example of a drilling system 100 for drilling an earth formation 101 to form a borehole 102 defining a wellbore 112. The drilling system 100 includes a drill rig 103 used to turn a drilling tool assembly 104 which extends downward into the borehole 102 and/or wellbore 112. The drilling tool assembly 104 may include a drill string 105, a bottomhole assembly ("BHA") 106, and a bit 110 attached to the downhole end of drill string 105. The wellbore 112 may be used to facilitate one or more of hydrocarbon recovery from the earth formation 101, carbon storage in the earth formation 101 (such as by injection of carbon dioxide into the earth formation 101, injection of other fluids into the earth formation 101, stimulation of geological formations for hydrogen generation and/or carbon dioxide storage, or other processes).

The drill string 105 may include several joints of drill pipe 108 connected end-to-end through tool joints 109. The drill string 105 transmits drilling fluid through a central bore and transmits rotational power from the drill rig 103 to the BHA 106. In some embodiments, the drill string 105 may further include additional components such as subs, pup joints, etc. The drill pipe 108 provides a hydraulic passage through which drilling fluid is pumped from the surface. The drilling fluid discharges through selected-size nozzles, jets, or other orifices in the bit 110 for the purposes of cooling the bit 110 and cutting structures thereon, and for lifting cuttings out of the borehole 102 or wellbore 112 as it is being drilled.

The BHA 106 may include the bit 110 or other components. An example BHA 106 may include additional or other components (e.g., coupled between to the drill string 105 and the bit 110). Examples of additional BHA components include drill collars, stabilizers, measurement-while-drilling ("MWD") tools, logging-while-drilling ("LWD") tools, downhole motors, underreamers, section mills, hydraulic disconnects, jars, vibration or dampening tools, other components, or combinations of the foregoing. The BHA 106 may further include a rotary steerable system (RSS). The RSS may include directional drilling tools that change a direction of the bit 110, and thereby the trajectory of the wellbore 112. At least a portion of the RSS may maintain a geostationary position relative to an absolute reference frame, such as gravity, magnetic north, and/or true north. Using measurements obtained with the geostationary position, the RSS may locate the bit 110, change the course of the bit 110, and direct the directional drilling tools on a projected trajectory.

In general, the drilling system 100 may include other drilling components and accessories, such as special valves (e.g., kelly cocks, blowout preventers, and safety valves). Additional components included in the drilling system 100 may be considered a part of the drilling tool assembly 104, the drill string 105, or a part of the BHA 106 depending on their locations in the drilling system 100.

The bit 110 in the BHA 106 may be any type of bit suitable for degrading downhole materials. For instance, the bit 110 may be a drill bit suitable for drilling the earth formation 101. Example types of drill bits used for drilling earth formations are fixed-cutter or drag bits. In other embodiments, the bit 110 may be a mill used for removing metal, composite, elastomer, other materials downhole, or combinations thereof. For instance, the bit 110 may be used with a whipstock to mill into casing 107 lining the wellbore 112. The bit 110 may also be a junk mill used to mill away tools, plugs, cement, other materials within the borehole 102, or combinations thereof. Swarf or other cuttings formed by use of a mill may be lifted to the surface, or may be allowed to fall downhole.

During drilling operations, a wellbore fluid (e.g., a drilling fluid) may be used to facilitate lubrication and cooling of the bit 110 and removal of cuttings of the earth formation 101 from the borehole 102 and/or wellbore 112. The drilling fluid may be configured to be circulated through the drill string 105, out of the drill string 105 through the bit 110, and into the annulus between the drill string 105 and the surfaces of the earth formation 101 defining the borehole 102 (or the wellbore 112). For example, a surface pump 114 may pump the drilling fluid from a mud pit 116 which holds the drilling fluid. In some embodiments, one or more additives may be added to the drilling fluid, such as by providing the one or more additives to the mud pit 116.

The wellbore fluid may include one or more emulsifiers formulated and configured to facilitate the formation of an emulsion (e.g., a dispersion of an immiscible liquid into another) by reducing the interfacial tension between two liquids. In some embodiments, the wellbore fluid includes an emulsifier configured to form a stable water-in-oil (e.g., invert) emulsion. In some embodiments, the emulsifier includes an amide (e.g., a bis-amide including two amide groups and a tertiary amine between the two amide groups; an imidazoline-amide including a tertiary amine, a terminal amide group, and a terminal imidazoline group). The tertiary amine may be bonded to a sulfonic acid group or a sulfonate group. In embodiments including a bis-amide, the two amide groups may be located at terminal portions of the bis-amide. In embodiments including a reaction product of an imidazoline-amide and the sultone, the emulsifier includes a tertiary amine, a terminal amide group, a terminal imidazoline group, and a sulfonic acid group bonded to the tertiary amine.

The wellbore fluid may include a base fluid, the emulsifier, and one or more additives. The one or more additives may include one or more of bridging materials, surfactants, viscosifiers, fluid loss materials, sealants, thinners (e.g., dispersion aids), weighting materials, filtration control agents, shale stabilizers, pH buffers, additional emulsifiers, corrosion inhibitors, scavengers, emulsion activators, gelling agents, shale inhibitors, defoamers, foaming agents, scale inhibitors, solvents, rheological additives, or other additives.

The wellbore fluid may include a drilling fluid, such as a non-aqueous-based drilling fluid (e.g., an oil-based drilling fluid, a synthetic-based drilling fluid). When lifting cuttings of the earth formation 101, the wellbore fluid may be referred to as a "drilling mud." In some embodiments, the wellbore fluid comprises a non-aqueous-based drilling fluid, such as an oil-based drilling fluid or a synthetic-based drilling fluid. In some such embodiments, the base fluid includes an oleaginous or oil-based fluid and may include a natural or synthetic oil. In some embodiments the oleaginous fluid is selected from the group consisting of at least one of diesel oil, mineral oil, a synthetic oil, (e.g., hydrogenated and unhydrogenated olefins including polyalpha olefins, linear and branched olefins), a mixture of alkanes with a carbon chain length ranging from $C_{10}$ to $C_{20}$ (e.g., SARALINE 185V, commercially available from Shell PLC of London, England), polydiorganosiloxanes, siloxanes, organosiloxanes, or esters of fatty acids (e.g., straight chained, branched and cyclical alkyl ethers of fatty acids). In some embodiments, the base fluid includes a mixture of $C_{16}$ to $C_{18}$ internal olefins (an alkene in which the double bond is within the carbon chain rather than at a terminal portion (at the alpha position) of the carbon chain).

An internal phase of an emulsion of the oleaginous or oil-based fluid may include one or more salts. The one or more salts may provide a desired density to the wellbore fluid and may also reduce the effect of the wellbore fluid on hydratable clays and shales the earth formation 101. The salts may include salts of one or more of sodium, calcium, aluminum, magnesium, zinc, potassium, strontium, or lithium, and salts of one or more of chlorides, bromides, carbonates, iodides, chlorates, bromates, formates, nitrates, oxides, phosphates, sulfates, silicates, or fluorides. In some embodiments, the salt includes a divalent halide, such as an alkaline earth halide (e.g., calcium chloride ($CaCl_2$)), calcium bromide ($CaBr_2$)), or a zinc halide. The salt may include cesium formate (HCOOR), sodium bromide (NaBr), potassium bromide (KBr), and cesium bromide (CsBr). The particular composition of the salt may be selected based on compatibility with the earth formation 101 and/or to match the brine phase of a completion fluid and/or a non-aqueous fluid. In some embodiments, the salt includes calcium chloride.

The salt may constitute from about 5.0 weight percent to about 30.0 weight percent of the wellbore fluid, such as from about 5.0 weight percent to about 10.0 weight percent, from about 10.0 weight percent to about 20.0 weight percent, or from about 20.0 weight percent to about 30.0 weight percent of the wellbore fluid. However, the disclosure is not so limited, and the weight percent of the salt and the water in the wellbore fluid may be different than that described.

As described above, the wellbore fluid may include the emulsifier including at least one emulsifier formulated and configured to reduce an amount of wellbore fluid (e.g., the drilling fluid) lost in the earth formation 101, such as during circulation of the wellbore fluid through the borehole 102 and/or wellbore 112 during drilling operations. For example, the emulsifier may facilitate formation of an emulsion by reducing the interfacial tension between the oleaginous phase and the aqueous phase of the wellbore fluid. In some embodiments, the emulsifier facilitates formation of a water-in-oil (e.g., an invert) emulsion.

The emulsifier may include an amide including a sulfonic acid group bonded to a tertiary amine (which may also be referred to herein as a "sulfonic acid-substituted amide"), the emulsifier including a reaction product of an amide (e.g., at least one of a bis-amide or an imidazoline-amide) and one or more sultones (e.g., 1,3-propane sultone, 1,4-butane sultone). The amide that is reacted with the one or more sultones used to form the emulsifier may include a reaction product of one or more polyamines and one or more fatty acids. The sultone may include an ester of hydroxyl sulfonic acids that have a sulfonyl oxy group in a cyclic (ring) structure. The sultone may include a sulfur atom in a cyclic structure, the sulfur atom double bonded to two oxygen atoms, single bonded to an oxygen atom that is part of the cyclic structure, and single bonded to a carbon atom of the cyclic structure.

The amide from which the emulsifier is formed may include a reaction product of one or more polyamines and one or more fatty acids and/or one or more vegetable oils (e.g., triglycerides, diglycerides, monoglycerides). In some embodiments, the amide includes a reaction product of one or more polyamines and one or more fatty acids. In some embodiments, the polyamine includes two terminal amine groups. In some embodiments, the polyamine includes a polyalkylamine including a compound having alternating amine and alkyl groups. The alkyl groups may be linear or branched. By way of non-limiting example, the polyalkylamine may include at least one of diethylenetriamine (DETA), triethylenetetramine (TETA), tetraethylene pentaamine (PETA), and pentaethylenehexamine (PEHA). In some embodiments, the polyalkylamine includes diethylenetriamine.

In some embodiments, the polyalkylamine includes a symmetrical compound. In some embodiments, the polyamine includes an alkanolamine (amino alcohol) including more than one amine group, such as aminoethylethanolamine (AEEA). In some embodiments, the polyamine includes dipropylenetriamine, propylenebutylenetriamine, spermidine, spermine, hexamethylenediamine, a polyethylenimine, or another polyamine. In some embodiments, the polyamine is selected from the group consisting of at least one of diethylenetriamine, triethylenetetramine, tetraethylene pentaamine, pentaethylenehexamine, and aminoethylethanolamine.

The fatty acid may be saturated or unsaturated, and may be linear, branched, or include one or more cyclic groups. By way of non-limiting example, the fatty acid may include one or more of valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, behenic acid, tricosylic acid, lignoceric acid, pentacosylic acid, cerotic acid, carboceric acid, montanic acid, nonacosylic acid, meliisic acid, lacceroic acid, psyllic acid, linolenic acid, stearidonic acid, eicosapentaenoic acid, cervonic acid, linoleic acid, linolelaidic acid, arachidonic acid, docosatetranoic acid, palmitoleic acid, vaccenic acid, paullinic acid, oleic acid, elaidic acid, erucic acid, crotonic acid, myristoleic acid, sapienic acid, gadoleic acid, or eicosenoic acid.

In some embodiments, the fatty acid is a saturated fatty acid (e.g., one or more of valeric acid, caproic acid, enanthic acid, caprylic acid, pelargonic acid, capric acid, undecylic acid, lauric acid, tridecylic acid, myristic acid, pentadecylic acid, palmitic acid, margaric acid, stearic acid, nonadecylic acid, arachidic acid, behenic acid, tricosylic acid, lignoceric acid, pentacosylic acid, cerotic acid, carboceric acid, montanic acid, nonacosylic acid, meliisic acid, lacceroic acid, psyllic acid). In other embodiments, the fatty acid is an unsaturated fatty acid (e.g., one or more of linolenic acid, stearidonic acid, eicosapentaenoic acid, cervonic acid, linoleic acid, linolelaidic acid, arachidonic acid, docosatetranoic acid, palmitoleic acid, vaccenic acid, paullinic acid, oleic acid, elaidic acid, erucic acid, crotonic acid, myristoleic acid, sapienic acid, gadoleic acid, and eicosenoic acid). The unsaturated fatty acid may be a monounsaturated fatty acid having one carbon to carbon double bond; a di-unsaturated fatty acid having two carbon to carbon double bonds; a tri-unsaturated fatty acid having three carbon to carbon double bonds; a tetra-unsaturated fatty acid having four carbon to carbon double bonds; a penta-unsaturated fatty acid having five carbon to carbon double bonds; a hexa-unsaturated fatty acid having six carbon to carbon double bonds; or a polyunsaturated fatty acid having more than six carbon to carbon double bonds.

In some embodiments, the fatty acid comprises, consists essentially of, or consists of tall oil fatty acid (TOFA) including one or more of oleic acid, linoleic acid, palmitic acid, and stearic acid. In some embodiments, the fatty acid comprises, consists essentially of, or consists of a mixture of oleic acid and linoleic acid. In some embodiments, the fatty acid comprises, consists essentially of, or consists of oleic acid.

In some embodiments, the amide is symmetrical. In some embodiments, the amide is a bis-amide including two amide groups and at least one central amine between the two amide groups. The amide groups may be terminal groups and may be bonded to the group corresponding to the fatty acid used to form the bis-amide.

Figure 2:
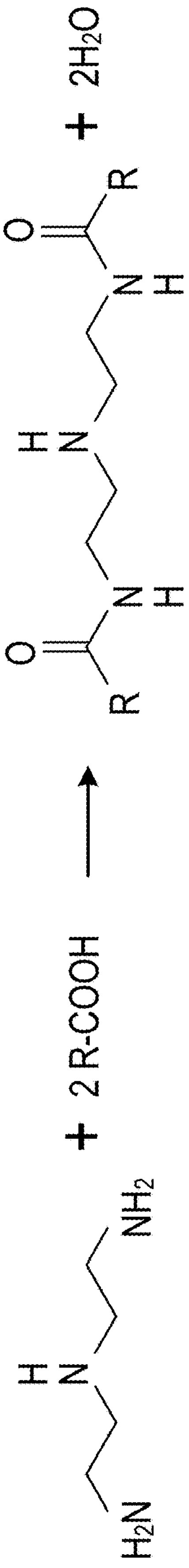
FIG. 2 is a reaction scheme of forming a bis-amide with a polyalkylamine and a fatty acid, according to at least one embodiment of the disclosure.

As described above, the amide used to form the emulsifier by reaction with the one or more sultones may include a reaction product of the polyamine and the fatty acid. In some embodiments, the reaction between the polyamine and the fatty acid is a condensation reaction resulting in one water molecule for every amide group formed (e.g., two water molecules when the reaction product is a bis-amide). For example, where the polyamine includes DETA, the amide may include a bis-amide formed according to the reaction scheme (I) illustrated below, which is also illustrated in FIG. 2:

(I)

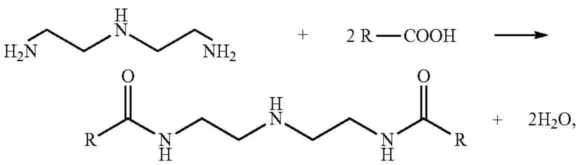

wherein R—COOH is a fatty acid, and R in the amide reaction product corresponds to the fatty acid reactant, but without the hydroxyl group of the fatty acid since the hydroxyl group is removed during the condensation reaction between the polyamine and the fatty acid. In other words, R may correspond to a fatty acid, but without the hydroxyl group of the fatty acid. For example, where the fatty acid includes oleic acid, R in the amide in reaction scheme (I) includes an oleate group (e.g., $CH_3(CH_2)_7CH{=}CH(CH_2)_7C({=}O)$—), wherein the carbonyl carbon is bonded to the nitrogen atom of the amide group. Similarly, R—N— in reaction scheme (I) includes a fatty acid amide group. As one example, where the fatty acid includes oleic acid, R—N— includes an oleamide group. In embodiments including a bis-amide, the fatty acids of the bis-amide may be the same and the amide groups may be the same. In other embodiments, the fatty acids of the bis-amide are different than one another and the corresponding amide groups are different than one another. In some embodiments, R is a $C_{16}$ to $C_{18}$ hydrocarbon, such as $C_{16}$ to $C_{17}$ hydrocarbon and may be saturated or unsaturated. In some embodiments, R is unsaturated.

As described above, in some embodiments, the amide may be formed by reacting one or more vegetable oils with the polyalkylamine in addition to or instead of one or more fatty acids. In some such embodiments, the reaction product of the vegetable oil and the polyalkylamine includes the same reaction product shown in reaction scheme (I) and further includes glycerol or an alcohol, depending on the vegetable oil (e.g., whether the vegetable oil is a triglyceride, a diglyceride, a monoglyceride, or includes a mixture thereof). The R group of the reaction product corresponds to the fatty acids of the vegetable oil reactant.

The amine number of the amide may depend on the number of free amines in the amide. The free amines may include the amine groups of the amide that are not amide groups. For example, in reaction scheme (I) above, the primary amines in the reactant may react with the fatty acid to form the amide groups, and the secondary amines may not react with the fatty acid and may not, therefore, form amide groups. The amine number of the amide may depend on the number of free amine groups in the amide. For example, the reaction product in reaction scheme (I) above includes one free amine group. In embodiments where the polyamine reactant includes TETA, the amide reaction product may include two free amine groups (and two amide groups). In embodiments where the polyamine reactant includes TEPA, the amide reaction product may include three free amine groups (and two amide groups). The amide may have an amine number within a range of from about 70 mg KOH/g to about 330 mg KOH/g, such as from about 70 mg KOH/g to about 90 mg KOH/g, from about 90 mg KOH/g to about 110 mg KOH/g, from about 110 mg KOH/g to about 150 mg KOH/g, from about 150 mg KOH/g to about 200 mg KOH/g, from about 200 mg KOH/g to about 250 mg KOH/g, from about 250 mg KOH/g to about 300 mg KOH/g, or from about 300 mg KOH/g to about 330 mg KOH/g. In some embodiments, the amine number of the amide is within a range of from about 85 mg KOH/g to about 95 mg KOH/g, such as about 90 mg KOH/g. However, the disclosure is not so limited, and the amine number of the amide may be different than that described.

The amide may be formed by, for example, mixing the polyalkylamine and the fatty acid and/or the vegetable oil with a solvent to form a mixture. The mixture may be stirred and heated to a first temperature within a range of from about 80° C. to about 100° C. (e.g., from about 80° C. to about 90° C.) for a duration within a range of from about 15 minutes to about 1 hour (e.g., for about 30 minutes). However, the disclosure is not so limited, and the mixture may be heated to a different temperature and/or stirred for a different duration. After heating the mixture to the first temperature, the mixture may be heated in an inert atmosphere to a second temperature within a range of from about 120° C. to about 180° C., such as from about 120° C. to about 150° C., or from about 150° C. to about 180° C. The mixture may be heated to the second temperature for a duration within a range of from about 15 hours to about 25 hours, such as from about 15 hours to about 20 hours, or from about 20 hours to about 25 hours.

Figure 3:
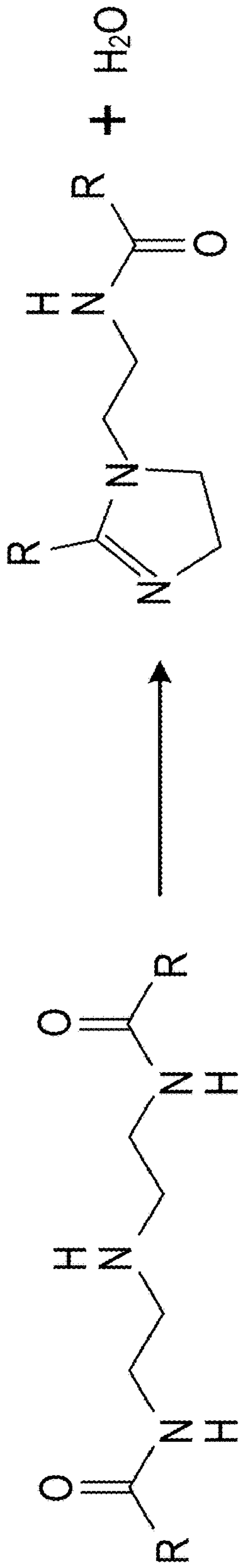
FIG. 3 is a condensation reaction of a bis-amide to form an imidazoline-amide and water, according to at least one embodiment of the disclosure.

In some embodiments, the amide reaction product condenses to form an imidazoline-amide, as shown in reaction scheme (II) illustrated below, which is also illustrated in FIG. 3.

(II)

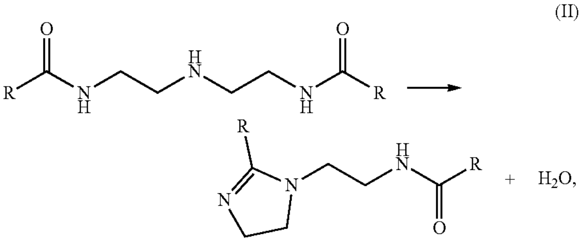

wherein R is the same as described above and corresponds to the fatty acid and/or the vegetable oil used to form the amide.

With reference to reaction scheme (II), condensation of the amide may result in the formation of an imidazoline-amide. The imidazoline-amide may include a terminal imidazoline group (e.g., a heterocyclic compound derived from the reduction of one of the two double bonds of an imidazole compound and including a five member cyclic structure including two nitrogen atoms, one of the nitrogen atoms double bonded to a carbon atom (e.g., part of an imine structure; C═N)), a terminal amide group, and a central amine group between the terminal imidazoline group and the terminal amide group. The imidazoline-amide may include one or more of a 2-imidazoline, a 3-imidazoline, or a 4-imidazoline. In other words, the imidazoline-amide may include some molecules having a 2-imidazoline group, a 3-imidazoline group, or a 4-imidazoline group, and may include other molecules including another of the 2-imidazoline group, the 3-imidazoline group, or the 4-imidazoline group. In some embodiments, the imidazoline-amide includes a 2-amidazoline amide. A carbon atom between the nitrogen atoms of the cyclic structure of the imidazoline-amide may be bonded to the R group, wherein the R group is the same as described above and corresponds to the fatty acid and/or the vegetable oil from which the amide is formed. In other words, the carbon atom of the imidazoline-amide that is bonded to the nitrogen atoms of the imidazoline structure may also be bonded to the R group.

In some embodiments, substantially all of the amide includes the bis-amide. In some embodiments, substantially all of the amide includes the imidazoline-amide. In some embodiments, the amide includes at least some of the bis-amide and at least some of the imidazoline-amide (the amide includes a mixture of the bis-amide and the imidazoline-amide). The relative amount of the imidazoline-amide to the bis-amide may depend on, for example, the water content of the amide mixture.

The amide may include from about 0.1 weight percent of the bis-amide to about 99.9 weight percent of the bis-amide, such as from about 0.1 weight percent to about 10.0 weight percent, from about 10.0 weight percent to about 20.0 weight percent, from about 20.0 weight percent to about 40.0 weight percent, from about 40.0 weight percent to about 60.0 weight percent, from about 60.0 weight percent to about 80.0 weight percent, or from about 80.0 weight percent to about 99.9 weight percent of the bis-amide. A remaining portion of the amide may include the imidazoline-amide. The amide may include from about 0.1 weight percent of the bis-amide to about 99.9 weight percent of the imidazoline-amide, such as from about 0.1 weight percent to about 10.0 weight percent, from about 10.0 weight percent to about 20.0 weight percent, from about 20.0 weight percent to about 40.0 weight percent, from about 40.0 weight percent to about 60.0 weight percent, from about 60.0 weight percent to about 80.0 weight percent, or from about 80.0 weight percent to about 99.9 weight percent of the imidazoline-amide.

As described above, the emulsifier may include a reaction product of the amide and one or more sultones. The emulsifier may include a reaction product of a sultone and at least one of (e.g., only one of, both of) a bis-amide or an imidazoline-amide. The emulsifier may include an amide including a tertiary amine bonded to a sulfonic acid group ($—SO_2—OH$; $SO_3H$) wherein the sulfur atom is double bonded to two oxygen atoms (S═O), single bonded to a hydroxyl group, and single bonded to a carbon chain (the length of which depends on the composition of the sultone). In some embodiments, the reaction product of the amide and the one or more sultones forms a sulfonate group ($—SO_3^-$), wherein the sulfur atom is double bonded to two oxygen atoms and single bonded to one oxygen atom. Thus, the reaction product may include a sulfonate group and/or a sulfonic acid group. The protonation of the sulfonate group (to form the sulfonic acid group) may depend on, for example, the pH of the solution in which the emulsifier is disposed.

In some embodiments, the sultone includes 1,3-propane sultone. In some embodiments, the sultone includes 1,4-butane sultone.

Figure 4:
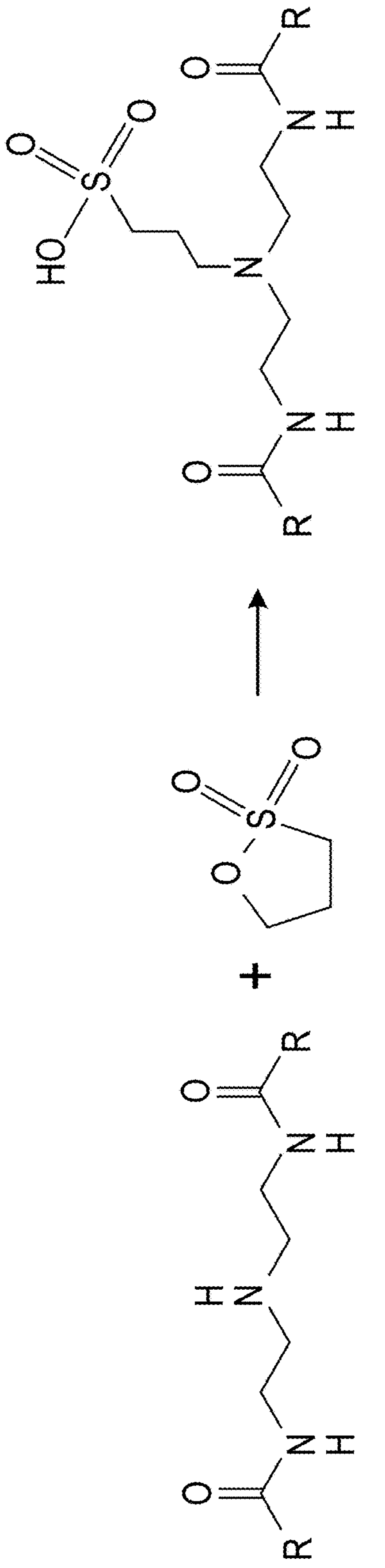
FIG. 4 is a reaction scheme of forming an emulsifier from a bis-amide and 1,3-propane sultone, according to at least one embodiment of the disclosure.

In some embodiments, the emulsifier includes a reaction product of a bis-amide and the one or more sultones. In some such embodiments, the emulsifier includes a bis-amide including two amide groups and a tertiary amine between the terminal amide groups and bonded to a sulfonic acid group. The two amide groups may be terminal amide groups. For example, where the emulsifier includes a reaction product of a bis-amide and the sultone includes 1,3-propane sultone, the emulsifier may have the general structure (III) shown below, which is also illustrated in FIG. 4.

(III)

Figure 5:
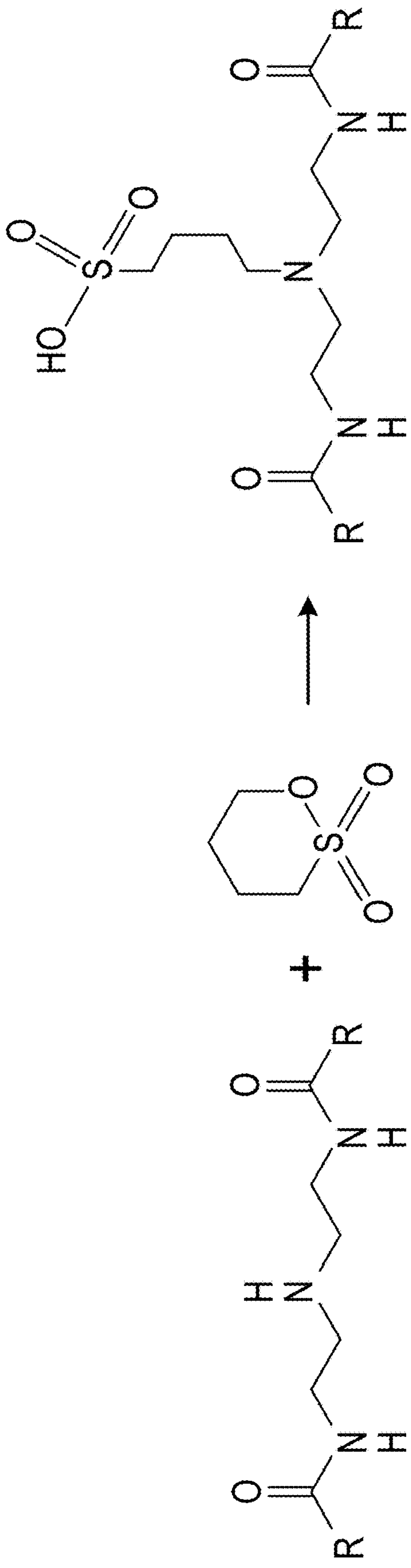
FIG. 5 is a reaction scheme of forming an emulsifier from a bis-amide and 1,4-butane sultone, according to at least one embodiment of the disclosure.

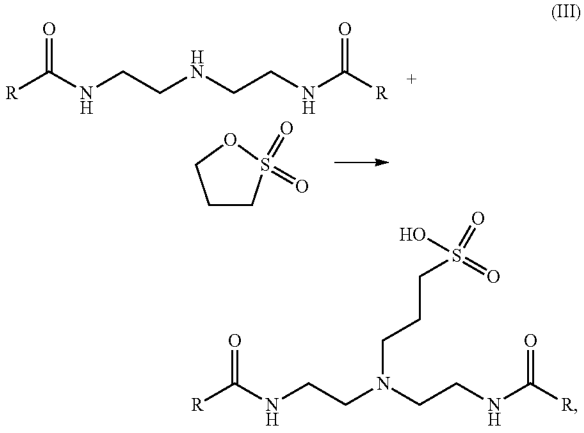

wherein R is the same as described above. The sulfonic acid group bonded to the tertiary amine may include a $—CH_2CH_2CH_2SO_3H$ group. Of course, where the sultone includes a sultone different than 1,3-propane sultone, the sulfonic acid group bonded to the tertiary amine may be different. For example, where the sultone includes 1,4-butane sultone, the sulfonic acid group bonded to the tertiary amine may include one more carbon atom than that illustrated in general structure (III) (e.g., the sulfonic acid group bonded to the tertiary amine may include a $—CH_2CH_2CH_2CH_2SO_3H$ group) and may have the general structure (IV) shown below, which is also illustrated in FIG. 5.

(IV)

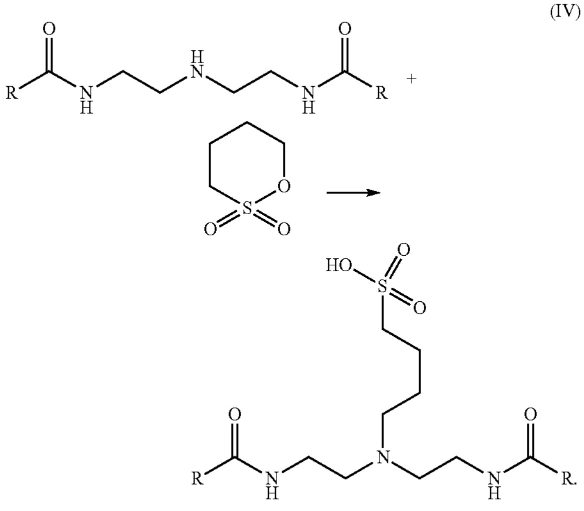

wherein R is the same as described above.

Figure 6:
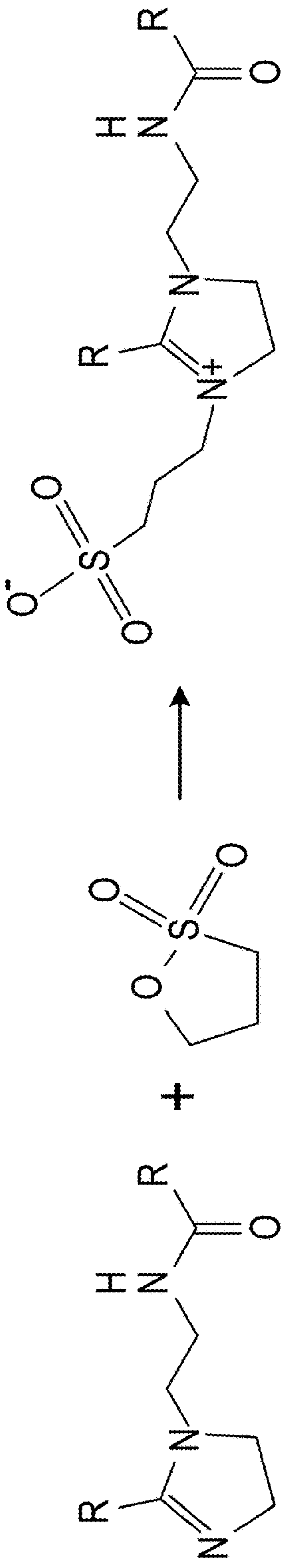
FIG. 6 is a reaction scheme of forming an emulsifier from an imidazoline-amide and 1,3-propane sultone, according to at least one embodiment of the disclosure.

In some embodiments, the emulsifier includes a reaction product of an imidazoline-amide and one or more sultones and the reaction product includes a sulfonate group. In some embodiments, the emulsifier includes an amide group, an imidazoline-amide group, and a tertiary amine between the amide group and the imidazoline-amide group. The tertiary amine may be between the amide group and the imidazoline-amide group and bonded to a sulfonic acid group. Where the emulsifier includes a reaction product of the imidazoline-amide and 1,3-propane sultone, the emulsifier may have the general structure (V) shown below, which is also illustrated in FIG. 6.

(V)

Figure 7:
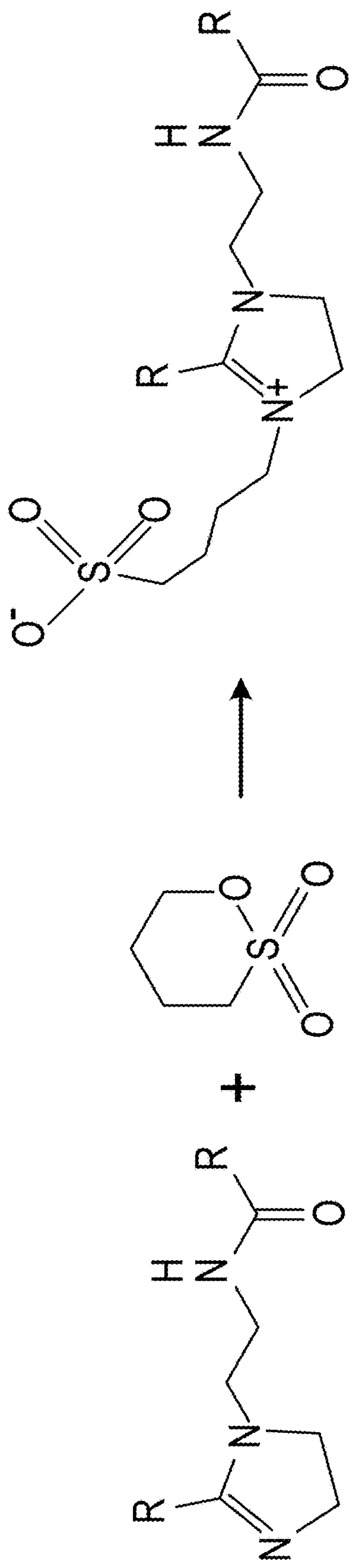
FIG. 7 is a reaction scheme of forming an emulsifier from an imidazoline-amide and 1,4-butane sultone, according to at least one embodiment of the disclosure.

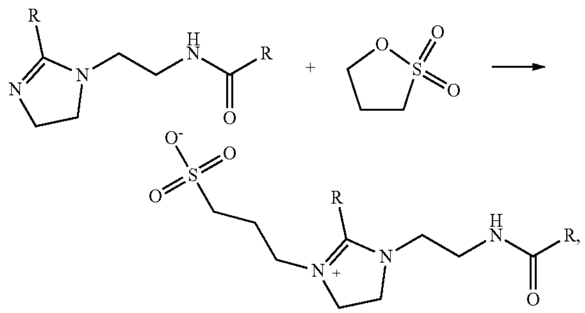

wherein R is the same as described above. As shown in general structure (V) above, the sulfonate group bonded to the tertiary amine may include a $—CH_2CH_2CH_2SO_3H$ group. Of course, where the sultone includes a sultone different than 1,3-propane sultone, the sulfonate group bonded to the tertiary amine may be different. For example, where the sultone includes 1,4-butane sultone, the sulfonate group bonded to the tertiary amine may include one more carbon atom than that illustrated in general structure (V) (e.g., the sulfonate group bonded to the tertiary amine may include a $—CH_2CH_2CH_2CH_2SO_3H$ group) and may have the general structure (VI) shown below, which is also illustrated in FIG. 7.

(VI)

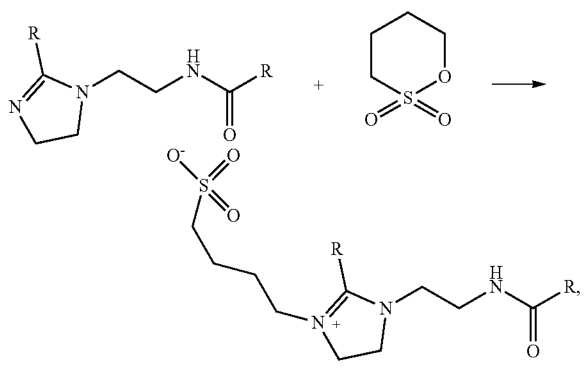

wherein R is the same as described above.

The emulsifier may include a mixture including a reaction product of a bis-amide and the sultone and a reaction product of an imidazoline-amide and the sultone. A weight ratio of the reaction product of the bis-amide and the sultone to the reaction product of the imidazoline-amide and the sultone may be within a range of from about 0.1:1.0 to about 1.0:10.0, such as from about 0.1:1.0 to about 0.5:1.0, from about 0.5:1.0 to about 1.0:1.0, from about 1.0:1.0 to about 1.0:2.0, from about 1.0:2.0 to about 1.0:4.0, from about 1.0:4.0 to about 1.0:6.0, from about 1.0:6.0 to about 1.0:8.0, or from about 1.0:8.0 to about 1.0:10.0. However, the disclosure is not so limited, and the ratio of the reaction product of the bis-amide and the sultone to the reaction product of the imidazoline-amide and the sultone may be different than that described.

The emulsifier may be an anionic emulsifier. For example, the sulfonic acid group and/or the sulfonate group bonded to the tertiary amine may exhibit anionic properties and impart anionic properties to the emulsifier. The anionic properties of the sulfonic acid group and/or the sulfonate group may facilitate improved properties of the emulsifier in a wellbore fluid.

The emulsifier may be formed by mixing the amide with a solvent at a temperature of at least about 50° C., such as at least about 70° C., or at least about 90° C. to form a mixture. The solvent may include, for example, dodecane or another hydrocarbon solvent, such as another alkane solvent (e.g., decane, hexane). The sultone may be added to the mixture and the mixture may be exposed to an inert gas (e.g., nitrogen gas). The mixture may be heated to a temperature of at least about 100° C., such as at least about 120° C., or at least about 130° C. In some embodiments, the mixture is heated to a temperature of about 130° C. for a duration (e.g., about 2 hours). In some embodiments, the completeness of the reaction is monitored by $^1H$ NMR analysis and monitoring the peak corresponding to the sultone content (e.g., when the peak corresponding to the sultone content decreased beyond a threshold, the sultone is reacted and the reaction is complete).

Accordingly, the emulsifier may include at least one amide group. An emulsifier composition may include an emulsifier including a bis-amide including a tertiary amine group bonded to a sulfonic acid group and/or an imidazoline-amide including a tertiary amine bonded to a sulfonate group.

The emulsifier may be present in the wellbore fluid at a concentration within a range of from about 2.85 kg/$m^3$ (about 1.0 pound per barrel (ppb)) to about 85.6 kg/$m^3$ (about 30.0 ppb), such as from about 2.85 kg/$m^3$ (about 1.0 ppb) to about 1.5 kg/$m^3$ (about 4.28 ppb), from about 1.5 kg/$m^3$ (about 4.28 ppb) to about 2.5 kg/$m^3$ (about 7.13 ppb), from about 2.5 kg/$m^3$ (about 7.13 ppb) to about 5.0 kg/$m^3$ (about 14.3 ppb), from about 5.0 kg/$m^3$ (about 14.3 ppb) to about 7.5 kg/$m^3$ (about 21.4 ppb), from about 7.5 kg/$m^3$ (about 21.4 ppb) to about 10.0 kg/$m^3$ (about 28.5 ppb), from about 10.0 kg/$m^3$ (about 28.5 ppb) to about 15.0 kg/$m^3$ (about 42.8 ppb), from about 15.0 kg/$m^3$ (about 42.8 ppb) to about 20.0 kg/$m^3$ (about 57.1 ppb), from about 20.0 kg/$m^3$ (about 57.1 ppb) to about 25.0 kg/$m^3$ (about 71.3 ppb), or from about 25.0 kg/$m^3$ (about 71.3 ppb) to about 85.6 kg/$m^3$ (about 30.0 ppb). In some embodiments, the emulsifier is present in the wellbore fluid within a range of from about 17.1 kg/$m^3$ (about 6.0 ppb) to about 32.2 kg/$m^3$ (about 12.0 ppb).

The emulsifier may be present in the wellbore fluid at a concentration within a range of from about 0.5 weight percent to about 10.0 weight percent, such as from about 0.5 weight percent to about 1.0 weight percent, from about 1.0 weight percent to about 2.0 weight percent, from about 2.0 weight percent to about 4.0 weight percent, from about 4.0 weight percent to about 6.0 weight percent, from about 6.0 weight percent to about 8.0 weight percent, or from about 8.0 weight percent to about 10.0 weight percent.

In some embodiments, the emulsifier is provided to the wellbore fluid as an emulsifier composition including, for example, a carrier fluid and/or a pour point depressant. For example, the emulsifier composition may include an oleaginous carrier fluid selected from the group consisting of at least one of diesel oil, mineral oil, a synthetic oil, a mixture of alkanes with a carbon chain length ranging from $C_{10}$ to $C_{20}$, a mixture of $C_{16}$ to $C_{18}$ internal olefins, or combinations thereof. The pour point depressant may include one or more glycol pour point depressants, such as one or more glycol ethers. However, the disclosure is not so limited, and in some embodiments, the emulsifier composition comprises, consists essentially of, or consists of the emulsifier and the acid.

As described above, the wellbore fluid may include one or more additives, which may be selected based on the desired properties of the wellbore fluid. By way of non-limiting example, the one or more additional additives may include one or more of surfactants, bridging materials, viscosifiers, wetting agents, thinners, weighting materials, filtration control agents, shale stabilizers, pH buffers, scavengers, emulsion activators, gelling agents, shale inhibitors, defoamers, foaming agents, scale inhibitors, solvents, rheological additives, or other additives that may be suitable depending on the particular operation.

The surfactants may include anionic surfactants, cationic surfactants, and/or non-ionic surfactants. The foaming agents may include a non-ionic surfactant including polymeric materials. The scale inhibitors may include an acrylic acid polymer, a maleic acid polymer, or a phosphonate. The solvents may include hydrocarbon solvents.

The bridging materials may include one or more of calcium carbonate, magnesium citrate, calcium citrate, calcium succinate, calcium maleate, calcium tartrate, magnesium tartrate, bismuth citrate, other suspended salts, mica, nutshells, fibers, or other building materials. In some embodiments, the building materials comprise calcium carbonate. The bridging material may be functionalized with one or more functional groups, such as one or more hydrophobic functional groups.

Viscosifiers of the wellbore fluid may include a material formulated and configured to increase the viscosity of the wellbore fluid and, optionally, to facilitate formation of a filtercake between the earth formation 101 and one or more of (e.g., each of) the drill string 105, casing 107, and liners. The viscosifier may include, for example, organic bentonite clay, an organic polymer (e.g., a cellulosic polymer), a polymer (e.g., a copolymer) formed from at least one acrylamide monomer and at least one sulfonated anionic monomer, or another polymer.

The viscosifier may constitute from about 0.5 weight percent to about 6.0 weight percent of the wellbore fluid, such as from about 0.5 weight percent to about 1.0 weight percent, from about 1.0 weight percent to about 2.0 weight percent, from about 2.0 weight percent to about 3.0 weight percent, or from about 3.0 weight percent to about 6.0 weight percent of the wellbore fluid. However, the disclosure is not so limited, and the weight percent of the viscosifier in the wellbore fluid may be different than that described.

Wellbore fluid thinners may include lignosulfates, lignitic materials, modified lignosulfonates, polyphosphates, tannin, and polyacrylates. The thinners may facilitate improved rheological properties of the wellbore fluid (e.g., a reduction in flow resistance) and a reduction in gel development. In addition, the thinner may reduce a thickness of filtercakes formed by the wellbore fluid, counteract the effects of salts, and reduce the effects of water on the earth formation 101.

Weighting materials (also referred to as “weighting agents”) may include one or more of barite ($BaSO_4$), iron oxide (e.g., $Fe_2O_3$, $Fe_3O_4$), calcium carbonate ($CaCO_3$), magnesium carbonate ($MgCO_3$), manganese oxide ($Mn_3O_4$), or combinations thereof. The weighting material may be present in the wellbore fluid and facilitate increasing the density of the wellbore fluid up to about 2.88 g/cm$^3$ (about 24 pounds per gallon (ppg)).

The pH buffer may include an amine stabilizer, such as one or more of triethanolamine ($C_6H_{15}NO_3$) (TEOA), methyldiethanolamine ($C_5H_{13}NO_2$) (MDEA), dimethylethanolamine ($C_4H_{11}NO$) (DMEA), diethanolamine ($C_4H_{11}NO_2$) (DEA), monoethanolamine (MEA), cyclic organic amines, sterically hindered amines, amides of fatty acid, or other suitable tertiary, secondary, or primary amines and ammonia. In some embodiments, the pH buffer includes magnesium oxide.

Wetting agents may include one or more alkanolamines, imidazolines, or amidoamines. Filtration control agents may include one or more of uintaite, amine-treated lignite, a polymeric additive, or another material. Shale stabilizers may include organophilic clays, cellulose derivates, or other materials. The scavenger may include, for example, zinc oxide, which may function as a hydrogen sulfide ($H_2S$) scavenger.

The gelling agent may include one or more of a clay and a crosslinked polyvinylpyrrolidone, an acrylamide copolymer, guar, sodium bentonite, or another material. Defoamers may include one or more of 2-octanol, oleic acid, paraffinic waxes, amide waxes, sulfonated oils, organic phosphates, silicone oils, mineral oils, or dimethylpolysiloxane.

The shale inhibitor may include one or more of amine tartaric salt, ammonium lauric salt, polyammonium, alkyl diammonium, an amphoteric polymer, an organosilicate polymer, a silicone polymer, hexamethylenediamine, bis-hexamethylene triamine, diaminocyclohexane, or another material. In some embodiments, the shale inhibitor includes an amine-based shale inhibitor.

A density of the wellbore fluid may be within a range of from about 1,080 kg/m$^3$ to about 2,500 kg/m$^3$, such as from about 1,080 kg/m$^3$ to about 1,200 kg/m$^3$, from about 1,200 kg/m$^3$ to about 1,400 kg/m$^3$, from about 1,400 kg/m$^3$ to about 1,600 kg/m$^3$, from about 1,600 kg/m$^3$ to about 1,800 kg/m$^3$, from about 1,800 kg/m$^3$ to about 2,000 kg/m$^3$, from about 2,000 kg/m$^3$ to about 2,200 kg/m$^3$, or from about 2,200 kg/m$^3$ to about 2,500 kg/m$^3$. However, the disclosure is not so limited, and the density of the wellbore fluid may be different than that described.

Forming the emulsifier from the sultone may facilitate forming the emulsifier with either of the amide (e.g., the bis-amide) and/or the imidazoline-amide. By way of comparison, amidoamine emulsifiers formed by reacting a bis-amide with a dicarboxylic acid (e.g., maleic acid), or a dicarboxylic anhydride (e.g., maleic anhydride) may detrimentally form imidazolines (e.g., imidazoline-amides), which are undesirable when forming the emulsifier from the amide and a dicarboxylic acid and/or dicarboxylic anhydride. The condensation reaction between the bis-amide and maleic anhydride may generate water. For the reaction kinetics to favor the formation emulsifier by the reaction of the bis-amide and the maleic anhydride, it is generally desired to remove the condensed water from the reaction solution. However, removal of the water may cause some of the bis-amide to condense to form an imidazoline-amide. The imidazoline-amide is undesirable because the imidazoline-amide causes rapid and poorly controlled decomposition of the maleic anhydride, and results in the formation of foam and degradation of the emulsifier quality. Accordingly, to reduce the imidazoline-amide content of the reaction solution, some of the water formed during the condensation reaction of the bis-amide and the maleic anhydride remains in the reaction solution. Some of the maleic anhydride reacts with the amide to form a maleic acid substituted amidoamine. However, some of the maleic anhydride hydrolyzes due to the presence of water and forms maleic acid rather than the desired emulsifier. The reaction between the maleic acid and the remaining amide may be completed, but requires elevated temperatures and a longer reaction time. Further, the elevated reaction temperatures may result in undesired by-products.

By way of comparison, forming the emulsifier with a sultone (rather than with a dicarboxylic acid or a dicarboxylic anhydride) may result in improved control of the reaction between the sultone and the at least one of the bis-amide or the imidazoline-amide. Since the sultone is not as reactive with water as the dicarboxylic anhydride (e.g., maleic anhydride), the water in the reaction solution does not have to be as precisely controlled as when reacting a bis-amide with a dicarboxylic anhydride. Further, the sultones exhibit a high reactivity with the amine group of the bis-amide and/or the imidazoline-amide and more preferentially react with the amine group of the amide than with water. The sultone may react with the amine at relatively lower temperatures than the maleic anhydride or the succinic anhydride. For example, the sultone is reactive with the amine group at room temperature (about 20° C.).

Figure 8:
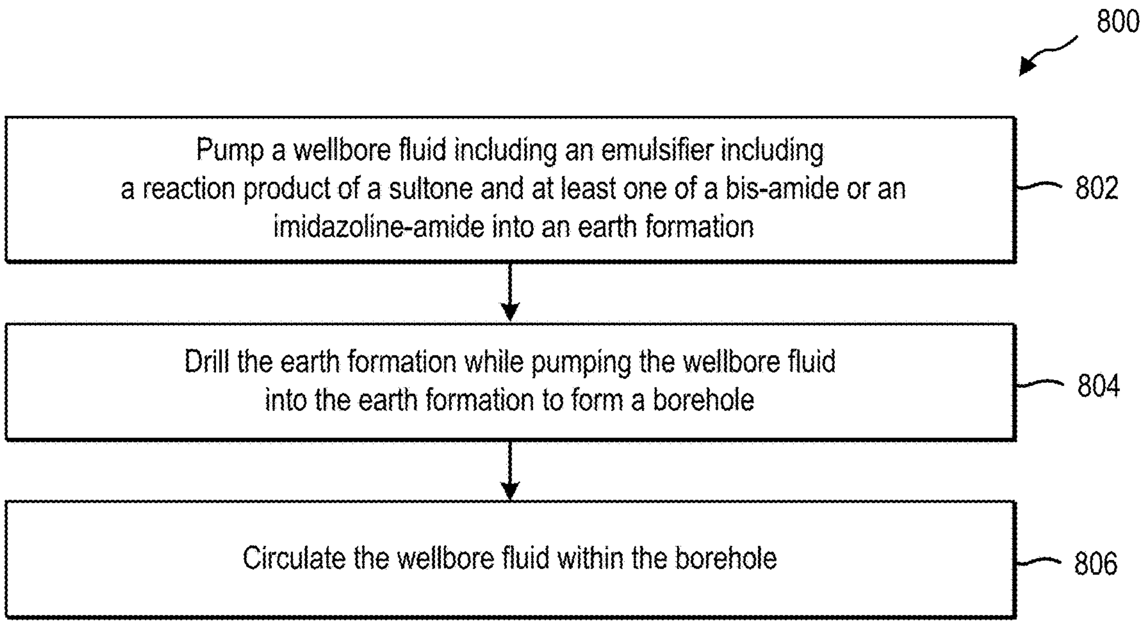
FIG. 8 is a simplified flow diagram illustrating a method of drilling a borehole, according to at least one embodiment of the disclosure.

FIG. 8 is a simplified flow diagram illustrating a method 800 of drilling a borehole using a drilling fluid including an emulsifier including a reaction product of a sultone and at least one of a bis-amide or an imidazoline-amide, according to at least one embodiment of the disclosure. The method 800 includes pumping a wellbore fluid including an emulsifier into an earth formation, as shown at act 802. The emulsifier may include one or more of the emulsifiers described above. For example, the emulsifier may include a reaction product of a sultone and an amide. The amide may include one or both of a bis-amide or an imidazoline-amide. The emulsifier may include at least one sulfonic acid group and/or at least one sulfonate group. For example, the emulsifier may include any of the emulsifiers shown in FIG. 4 through FIG. 7. In some embodiments, the wellbore fluid comprises a drilling fluid.

The method 800 may include drilling the earth formation while pumping the wellbore fluid into the earth formation to form a borehole, as shown in act 804. For example, the wellbore fluid may be pumped from the surface of the earth formation, through the drill string 105, out of the bit 110, and through an annulus between the drill string 105 and the earth formation 101. In some embodiments, the wellbore fluid forms a stable emulsion (e.g., a water-in-oil emulsion) while the wellbore fluid is circulated through the borehole 102. The wellbore fluid may facilitate removal of cuttings from the wellbore as the wellbore fluid circulates through the wellbore.

The method 800 may further include circulating the wellbore fluid through the borehole while drilling the earth formation, as shown at act 806. Circulating the wellbore fluid through the borehole may include pumping the wellbore fluid through the drill string 105, out of the bit 110, and through the annulus between the drill string 105 and the earth formation 101.

Figure 9:
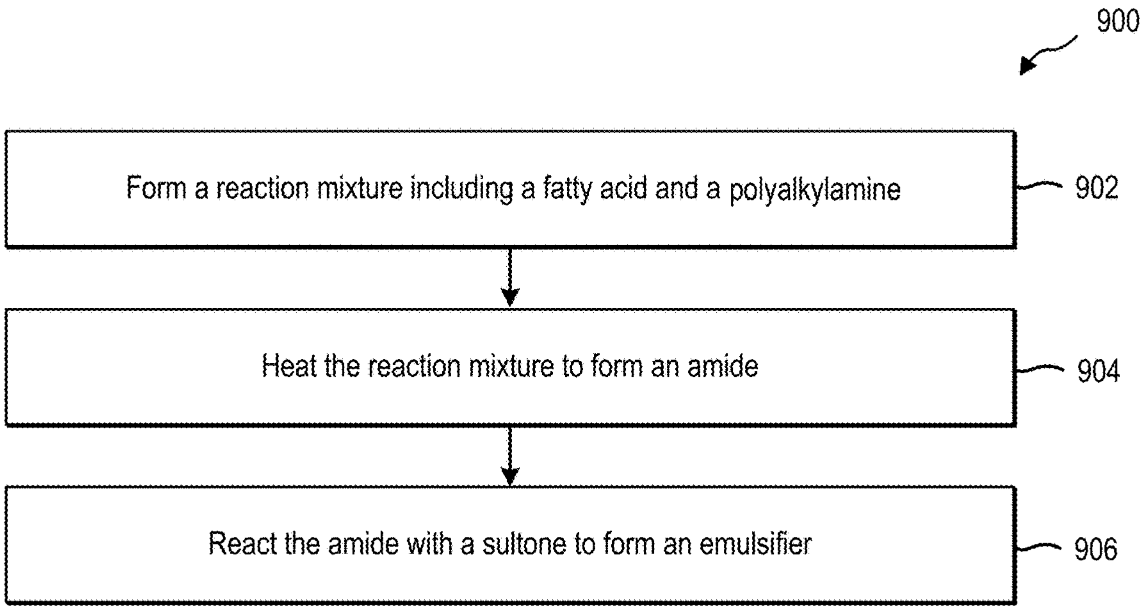
FIG. 9 is a simplified flow diagram illustrating a method of forming an emulsifier, according to at least one embodiment of the disclosure.

FIG. 9 is a simplified flow diagram illustrating a method 900 of forming an emulsifier including a reaction product of a sultone and at least one of a bis-amide or an imidazoline-amide, according to at least one embodiment of the disclosure. The method 900 may include forming a reaction mixture including a fatty acid and a polyalkylamine, as shown in act 902. The fatty acid and the polyalkylamine may include one or more of the respective fatty acids and polyalkylamines described above.

The method 900 may further include heating the reaction mixture to form an amide, as shown in act 904. Heating the reaction mixture may include heating the reaction mixture to a temperature greater than about 60° C., such as greater than about 80° C., greater than about 100° C., or greater than about 120° C. The amide may include one or both of a bis-amide, as described above with reference to FIG. 2. At least some of the bis-amide may condense to form an imidazoline-amide, as described above with reference to FIG. 3.

With continued reference to FIG. 9, the method 900 may further include reacting the amide with a sultone to form an emulsifier, as shown in act 906. The sultone may include one or more of the sultones described above. The emulsifier may include an amide including a central amine (e.g., a tertiary amine) bonded to a sulfonic acid group and/or a sulfonate group. The amine may be bonded to two amide groups or may be bonded to an amide group and an imidazoline group. In some embodiments, the emulsifier includes a mixture of emulsifiers including bis-amides with a sulfonic acid group and an imidazoline-amide with a sulfonate group.

EXAMPLES

Example 1

A bis-amide was formed by reacting tall oil fatty acid (including oleic acid and linoleic acid) with diethylenetriamine in a 1 L glass reactor under nitrogen flow. About 281 grams of the tall oil fatty acid was mixed with about 51.58 grams of the diethylenetriamine to form a reaction mixture. The reaction mixture was heated to a temperature between about 80°C and about 90°C for about 30 minutes while mixing. After about 30 minutes, the glass reactor was closed and heated to about 130° C. for about 20 hours. After about 20 hours, the glass reactor was opened to air and the water vapor was removed by passing a stream of nitrogen for about 60 minutes through the glass reactor. After cooling to room temperature, 1H NMR spectroscopy was used to confirm the formation of a pure bis-amide of FIG. 2.

Example 2

The same tall oil fatty acid of Example 1 was mixed with diethylenetriamine in a 1 L glass reactor to form an imidazoline-amide. About 281 grams of the tall oil fatty acid was mixed with about 51.58 grams of the diethylenetriamine to form a reaction mixture. The reaction mixture was heated to a temperature between about 80°C and about 90°C for about 30 minutes while mixing while the glass reactor was open to air. The reactor was flushed with a constant nitrogen flow and heated to about 160° C. for about 21 hours. After the reaction was complete, $^{1}H$ NMR spectroscopy was used to confirm the formation of the imidazoline-amide of FIG. 3. The $^{13}C$ NMR spectra show signals at 173.7 ppm, corresponding to the carbonyl of the bis-amide.

Figure 10A:
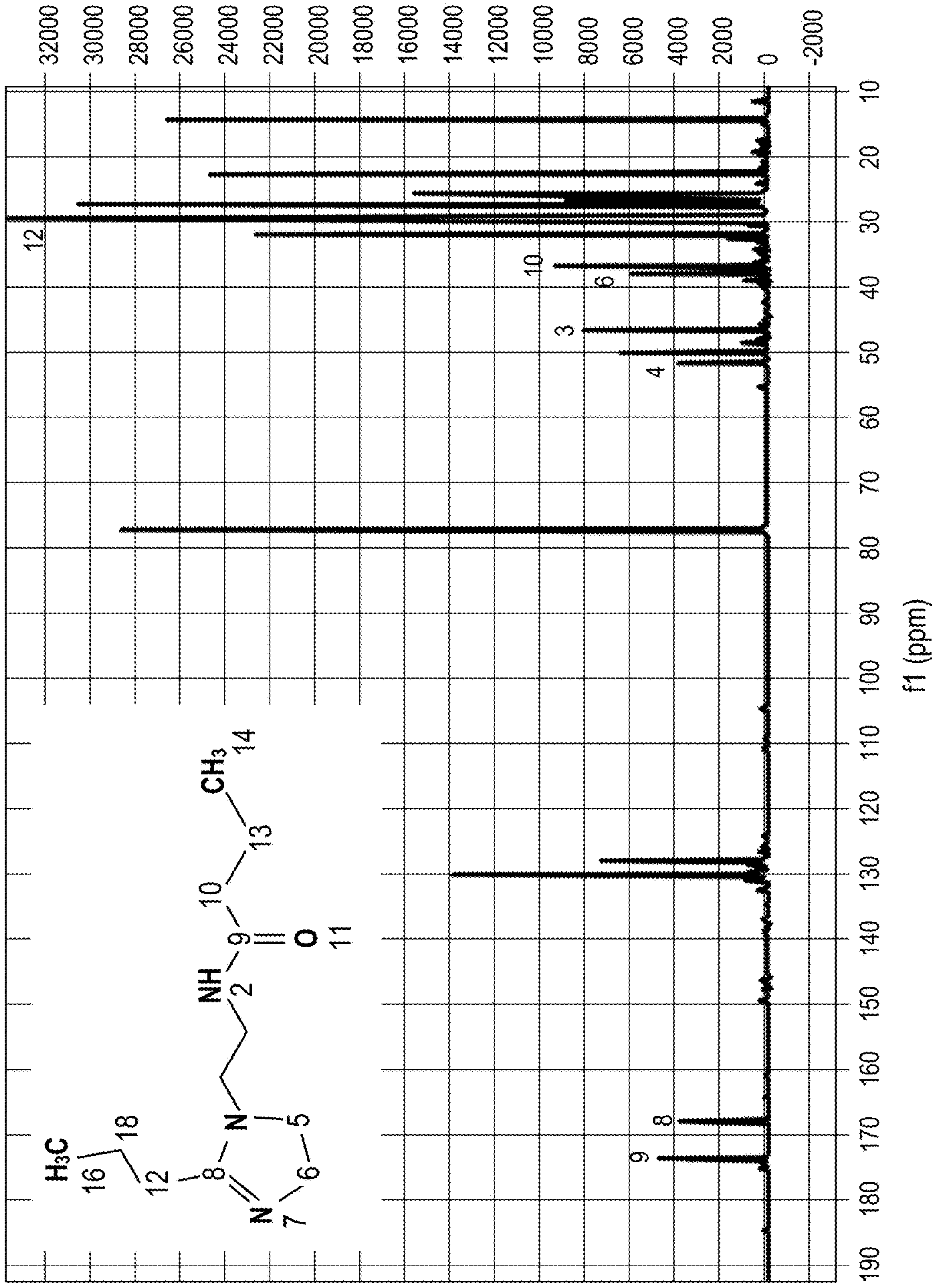
FIG. 10A is a $^{13}C$ NMR spectra of an imidazoline-amide formed by reacting tall oil fatty acid with diethylenetriamine.
Figure 10B:
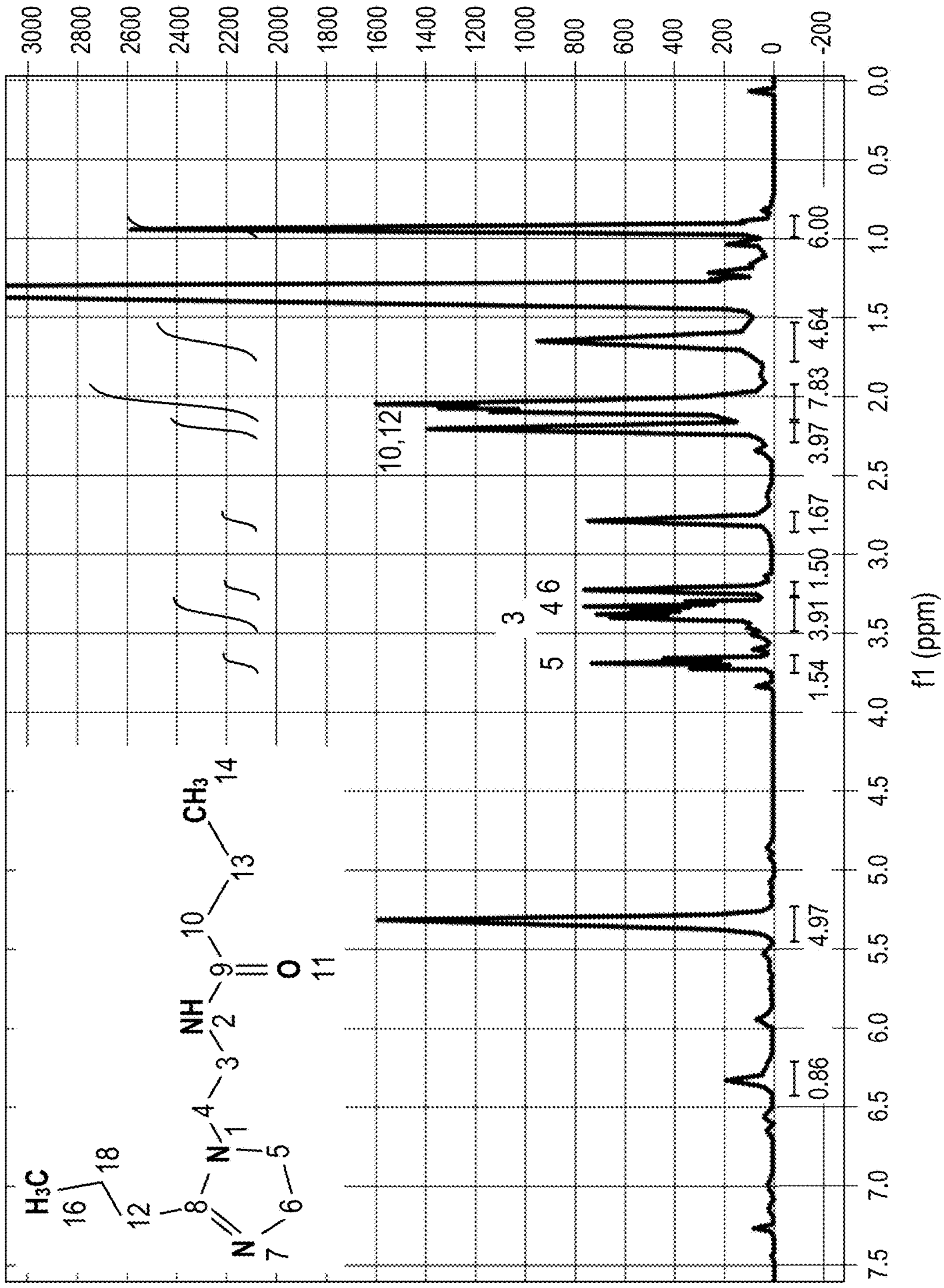
FIG. 10B is a $^{1}H$ NMR of the imidazoline-amide of FIG. 10A.

FIG. 10A is a $^{13}C$ NMR spectra and FIG. 10B is a $^{1}H$ NMR spectra of the reaction product. With reference to FIG. 10A, the $^{13}C$ NMR spectra shows two characteristic signals at 173.43 ppm, corresponding to the secondary amide carbonyl (corresponding to carbon 9 in the $^{13}C$ NMR spectra), and a signal at 167.7 ppm corresponding to the quaternary carbon of the imidazoline-amide (corresponding to carbon 8 in the $^{13}C$ NMR spectra).

Example 3

The reaction product of Example 1 was reacted with 1,3-propane sultone to form an emulsifier. About 50 grams of the bis-amide reaction product of Example 1 was mixed with dodecane in a 0.5 L glass reactor to form a mixture. The mixture was heated to about 90° C., followed by addition of about 9.87 grams of 1,3-propane sultone to form a reaction mixture. The glass reactor was purged with a constant nitrogen flow and stirred with a magnetic stirrer. The reaction temperature was maintained between about 80° C. and about 90° C. for about 30 minutes. After about 30 minutes, the reaction mixture was heated to about 130° C. for about 2 hours. The completeness of the reaction was monitored by measuring the residual sultone peak (at about 4.5 ppm) in the $^1$H NMR of the reaction mixture. The reaction product had the structure of the reaction product illustrated in FIG. 4.

Figure 11:
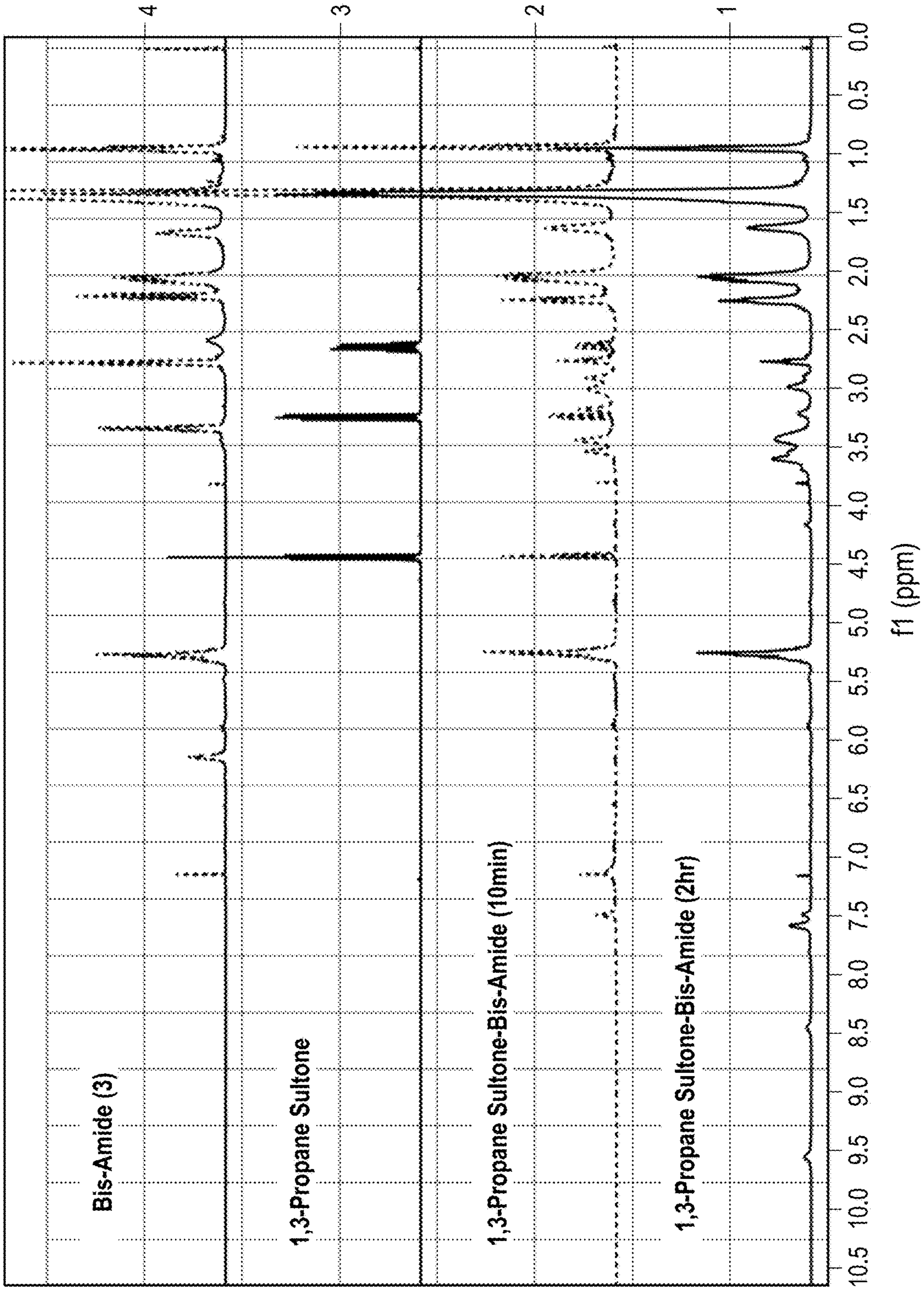
FIG. 11 is a $^{1}H$ NMR spectra of a bis-amide, 1,3-propane sultone, and a reaction product of the bis-amide and the 1,3-propane sultone after reacting for 10 minutes and after reacting for 2 hours.

FIG. 11 shows $^1$H NMR spectra of bis-amide reactant, the 1,3-propane sultone reactant, and the $^1$H NMR spectra of the reaction mixture after reacting at about 130° C. for about 10 minutes, and after reacting for about 2 hours. With reference to FIG. 11, the $^1$H NMR spectra of the 1,3-propane sultone reactant includes a peak at about 4.5 ppm corresponding to the sultone. After about 10 minutes, the reaction solution still included residual sultone, indicating that the reaction was not complete. After about 2 hours, the $^1$H NMR spectra did not include a peak at about 4.5 ppm, indicating that the 1,3-propane sultone had reacted.

Example 4

Figure 12:
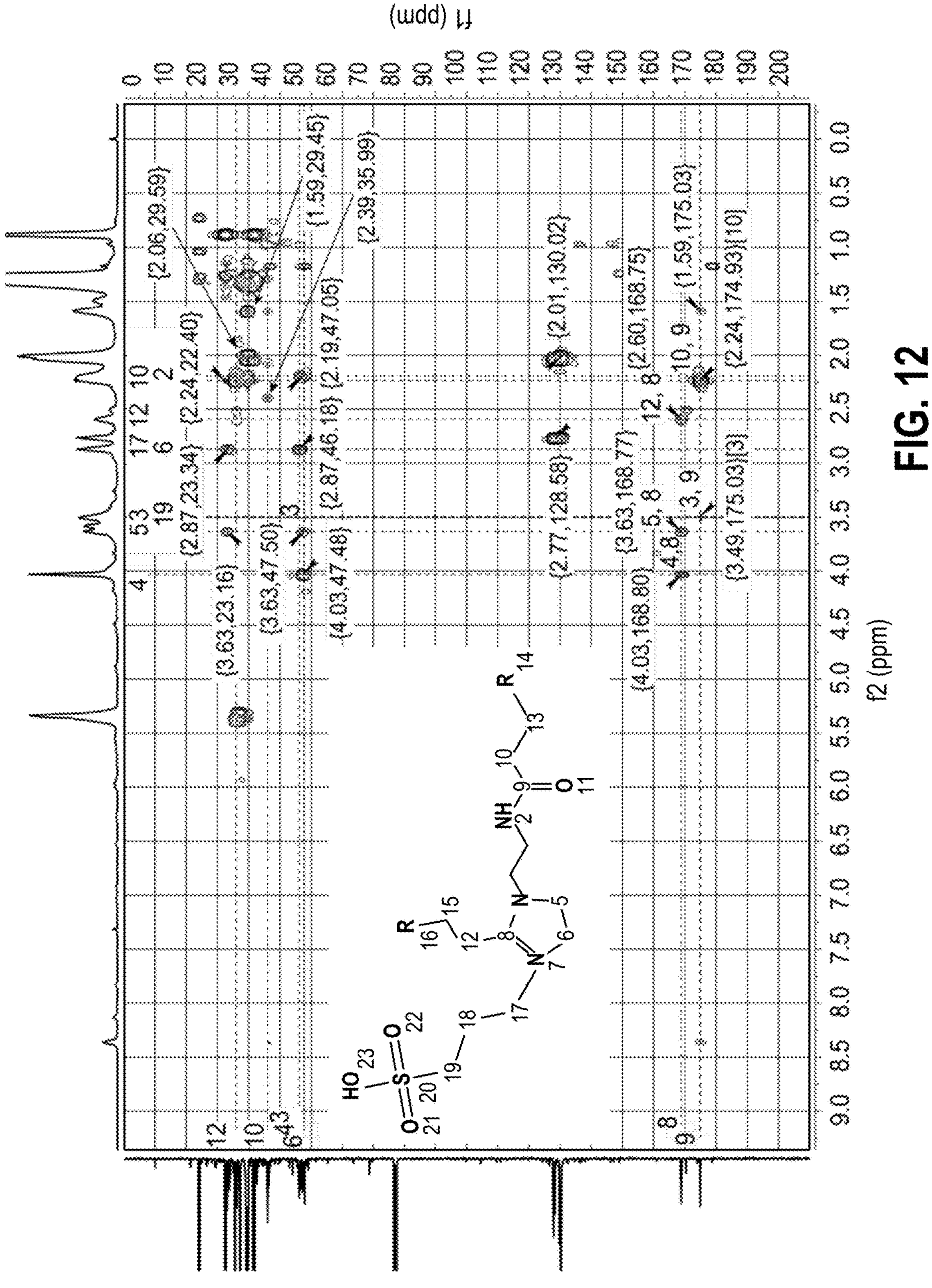
FIG. 12 is a heteronuclear multiple-bond correction (HMBC) spectra of a reaction product of an imidazoline-amide and 1,3-propane sultone.

The imidazoline-amide formed during Example 2 was reacted with 1,3-propane sultone to form the reaction product shown in FIG. 6. FIG. 12 is a heteronuclear multiple-bond correlation (HMBC) spectra of the reaction product. With reference to FIG. 12, the HMBC spectra confirms the presence of the imidazoline-amide reaction product including a tertiary amine, an imidazoline bonded to the tertiary amine and including a sulfonate group, and an amide bonded to the tertiary amine.

Example 5

The performance of emulsifiers formed according to embodiments described herein in drilling fluids was compared to the performance of amidoamine emulsifiers. The composition of the drilling fluid is shown in Table 1 below. The emulsifiers were provided in an emulsifier composition and included 50 percent active emulsifier (e.g., for the 7.0 grams of emulsifier composition in the drilling fluid, the emulsifier composition included about 3.5 grams of the emulsifier). The drilling fluids had a density of about 14.3 pounds per barrel (about 40.9 kg/m$^3$) and included about 77 percent oil by volume and about 23 percent water by volume.

TABLE 1

| Material | Weight (g) |
|---|---|
| Isomerized $C_{16}$-$C_{18}$ alpha olefin base oil | 141.0 |
| Emulsifier composition | 7.0 |
| Alcohol ethoxylate surfactant | 3.5 |
| Non-ionic surfactant | 1.10 |
| Organophilic clay | 0.50 |
| Lime | 5.0 |
| $CaCl_2$ brine | 77.6 |
| Rheology additive | 12.0 |
| Filtration control additive | 0.2 |
| Fluid loss additive | 1.7 |
| Barite | 352.0 |

The tested emulsifiers included an amidoamine emulsifier, an emulsifier including a reaction product of a bis-amide and 1,3-propane sultone (as shown in FIG. 4; emulsifier 1), an emulsifier including a reaction product of a bis-amide and 1,4-butane sultone (as shown in FIG. 5; emulsifier 2), and an emulsifier including a reaction product of an imidazoline-amide and 1,3-propane sultone (as shown in FIG. 6; emulsifier 3). The performance of each drilling fluid was compared by measuring the viscosity of the drilling fluids at about 40° F. (about 4.4° C.) and about 150° F. (about 65.6° C.) using a rotational couette viscometer at different rotation speeds (RPM) after hot rolling at about 150° F. (about 65.6° C.) for about 16 hours. In addition, the gel strength of the drilling fluids and the fluid loss of the drilling fluids when exposed to HPHT testing at a differential pressure of about 500 psi (about 3.45 MPa) at about 280° F. (about 137.8° C.) were also tested. The fluid loss after hot rolling for each of the drilling fluids was also measured and compared. In the fluid loss test, the drilling fluids were exposed to HPHT testing at a differential pressure of about 500 psi (about 3.45 MPa) for about 60 minutes according to an API HPHT fluid-loss test. According to the API HPHT fluid-loss test, the fluid loss was measured as the volume of the filtrate fluid that passed through a WFAO-A disk after 60 minutes. The results are shown in Table 2 below.

TABLE 2

| | Amidoamine emulsifier | | Emulsifier 1 | | Emulsifier 2 | | Emulsifier 3 | |
|---|---|---|---|---|---|---|---|---|
| Rheology temperature (° F.) | 40 | 150 | 40 | 150 | 40 | 150 | 40 | 150 |
| R600, ° VG | 174 | 56 | 158 | 51 | 189 | 57 | 183 | 58 |
| R300, ° VG | 96 | 33 | 88 | 29 | 101 | 34 | 104 | 33 |
| R200, ° VG | 69 | 26 | 62 | 22 | 70 | 25 | 73 | 24 |
| R100, ° VG | 39 | 17 | 33 | 13 | 39 | 15 | 40 | 14 |
| R6, ° VG | 9.0 | 9.0 | 5.0 | 5.0 | 6.0 | 6.0 | 6.0 | 4.0 |
| R3, ° VG | 7.0 | 9.0 | 3.0 | 5.0 | 5.0 | 6.0 | 5.0 | 4.0 |
| Plastic viscosity, cP | 78 | 23 | 70 | 22 | 88 | 23 | 79 | 25 |
| Yield point, lb/100 ft$^2$ | 18 | 10 | 18 | 7 | 13 | 11 | 25 | 8 |
| Low-shear yield point, lb/100 ft$^2$) | 5 | 9 | 1 | 5 | 4 | 6 | 4 | 4 |
| 10-sec gel, lb/100 ft$^2$ | 10 | 16 | 5 | 5 | 6 | 7 | 5 | 4 |
| 10-min gel, lb/100 ft$^2$ | 27 | 37 | 8 | 24 | 10 | 25 | 9 | 14 |
| Electrical stability (at 150° F.), V | — | 512 | — | 454 | — | 440 | — | 676 |
| HPHT Temp, ° F. | — | 280 | — | 280 | — | 280 | — | 280 |
| HPHT fluid loss, mL | — | 1.7 | — | 0 | — | 0.4 | — | 0.9 |
| Water in HPHT filtrate, mL | — | 0 | — | 0 | — | 0 | — | 0 |

With reference to Table 2, the fluid loss appeared to be better for the emulsifiers including the anionic sulfonic acid group and/or sulfonate group compared to the amidoamine emulsifier. The fluid loss was tested at about 280° F. (about 137.8° C.) after hot rolling for about 16 hours. The rheology of the drilling fluids including the different emulsifiers appeared to be relatively similar and within acceptable ranges for drilling fluids. The rheology of the drilling fluids including the sulfonic group and/or sulfonate group appeared to be relatively similar to the rheology of the drilling fluid including the amidoamine emulsifier.

The drilling fluids were also tested at a temperature of about 330° F. (about 165.6° C.) to test the performance of the emulsifiers at higher temperatures. The drilling fluids including the emulsifiers were hot rolled for about 16 hours at about 330° F. (about 165.6° C.). After hot rolling, the fluid loss properties of the drilling fluids were measured. The results are shown in Table 3 below.

TABLE 3

| | Amidoamine emulsifier | | Emulsifier 1 | | Emulsifier 2 | | Emulsifier 3 | |
|---|---|---|---|---|---|---|---|---|
| Rheology temperature (° F.) | 40 | 150 | 40 | 150 | 40 | 150 | 40 | 150 |
| R600, ° VG | 199 | 63 | 223 | 91 | 222 | 97 | 255 | 78 |
| R300, ° VG | 111 | 37 | 124 | 52 | 125 | 55 | 142 | 48 |
| R200, ° VG | 78 | 27 | 88 | 38 | 88 | 41 | 100 | 35 |
| R100, ° VG | 43 | 16 | 48 | 24 | 49 | 27 | 55 | 22 |
| R6, ° VG | 6.0 | 6.0 | 6.0 | 11.0 | 6.0 | 14.0 | 9.0 | 11.0 |
| R3, ° VG | 4.0 | 7.0 | 5.0 | 11.0 | 5.0 | 14.0 | 7.0 | 11.0 |
| Plastic viscosity, cP | 88 | 26 | 99 | 39 | 97 | 42 | 113 | 30 |
| Yield point, lb/100 $ft^2$ | 23 | 11 | 25 | 13 | 28 | 13 | 29 | 18 |
| Low-shear yield point, lb/100 $ft^2$) | 2 | 8 | 4 | 11 | 4 | 14 | 5 | 11 |
| 10-sec gel, lb/100 $ft^2$ | 6 | 7 | 5 | 11 | 6 | 14 | 9 | 9 |
| 10-min gel, lb/100 $ft^2$ | 14 | 38 | 15 | 59 | 17 | 79 | 18 | 38 |
| Electrical stability (at 150° F.), V | — | 320 | — | 230 | — | 300 | — | 470 |
| HPHT Temp, ° F.) | — | 330 | — | 330 | — | 330 | — | 330 |
| HPHT fluid loss, mL | — | 1.8 | — | 2 | — | 2.4 | — | 1.9 |
| Water in HPHT filtrate, mL | — | 0 | — | 0 | — | 0 | — | 1 |

With reference to Table 3, the drilling fluid including emulsifier 1 exhibited comparable products to the drilling fluid including the amidoamine emulsifier, and also exhibited a higher (better) low-shear rate viscosity (LSRV) at about 150° F. (about 65.6° C.) than the drilling fluid including the amidoamine emulsifier, which is typically difficult to achieve in drilling fluid compositions without increasing the thickness of the drilling fluid at lower temperatures (e.g., at temperature of about 40° F. (about 4.4° C.). In addition, the R600 of the drilling fluids at about 40° F. (about 4.4° C.) including emulsifiers 1 through 3 was comparable to the drilling fluid including the amidoamine emulsifier. With continued reference to Table 3, the drilling fluid including emulsifier 1 and the drilling fluid including emulsifier 3 exhibited relatively similar rheological and fluid loss properties, indicating that the ratio of the bis-amide to the imidazoline-amide used to form the emulsifier has little effect on the properties and performance of the resulting emulsifier. The drilling fluid formed with emulsifier 2, which was formed from 1,4-butane sultone exhibited a different LSRV compared to drilling fluids 1 and 3, which were formed from 1,3-propane sultone, but the rheology of the drilling fluid may be adjusted with rheology modifiers or other additives. Each of the drilling fluids formed from emulsifier 1, emulsifier 2, and emulsifier 3 exhibited low fluid loss and did not include water in the filtrate, indicating excellent high temperature stability of the drilling fluids formed with the emulsifiers.

Example 6

The performance of a drilling fluid including an emulsifier formed by reacting a bis-amide with 1,3-propane sultone was tested. The composition of the drilling fluid is shown in Table 4 below. The emulsifier in Table 4 was the reaction product of the bis-amide and 1,3-propane sultone. The drilling fluid had a specific gravity of about 1.717, a density of about 14.3 pounds per barrel (about 40.9 $kg/m^3$), and included about 77 percent oil by volume and about 23 percent water by volume.

TABLE 4

| Material | Volume (mL) | Weight (g) |
|---|---|---|
| Isomerized $C_{16}$-$C_{18}$ alpha olefin base oil | 174.5 | 136.1 |
| Emulsifier | 9.444 | 8.5 |
| Flat rheology conditioner | 4.444 | 4.0 |
| Non-ionic surfactant | 2.989 | 2.67 |
| Organophilic clay | 0.313 | .050 |
| Lime | 2.137 | 5.0 |
| $CaCl_2$ brine | 62.84 | 77.3 |
| Rheology additive | 5.417 | 13.00 |
| Filtration control additive | 0.75 | 0.8 |
| Fluid loss additive | 2.667 | 2.4 |
| Barite | 84.48 | 350.6 |

The emulsifier was added to the drilling fluid of Table 4. The rheological properties, fluid loss, and other properties of the drilling fluid were measured at about 40° F. (about 4.4° C.) and about 150° F. (about 65.6° C.) after heat aging for about 16 hours, and after heat aging for about 3 days and 16 hours (hot rolling and static aging). The results of the rheological testing and fluid loss testing are shown in Table 5 below.

TABLE 5

| | Heat aging temperature, (° F.) | | | |
|---|---|---|---|---|
| | 350 | | 350 | |
| | Heat aging | | | |
| Static/rolling | 16 hours Dynamic hot rolling | | 3 days + 16 hours Static aging | |
| Rheology temperature, (° F.) | 40 | 150 | 40 | 150 |
| R600, °VG | 222 | 79 | 226 | 86 |
| R300, °VG | 127 | 49 | 128 | 54 |
| R200, °VG | 91 | 37 | 82 | 42 |
| R100, °VG | 51 | 25 | 51 | 28 |
| R6, °VG | 7.2 | 8.0 | 8.0 | 13.0 |
| R3, °VG | 5.2 | 8.0 | 6.0 | 12.0 |
| Plastic viscosity, cP | 95 | 30 | 98 | 32 |
| Yield point, lb/100 $ft^2$ | 32 | 19 | 30 | 22 |
| Low-shear yield point, lb/100 $ft^2$) | 3 | 8 | 4 | 11 |
| 10-sec gel, lb/100 $ft^2$ | 9 | 8 | 9 | 22 |
| 10-min gel, lb/100 $ft^2$ | 14 | 38 | 32 | 51 |
| [HTHP]]HPHT Temp, ° F. | — | 325 | | 325 |
| [[HTHP]HPHT fluid loss, mL | — | | | 13.6 |
| Water in [[HTHP]]HPHT filtrate, mL | — | | | 0.8 |
| Free oil, mL | — | | | 50 |

With reference to Table 5, the drilling fluid including the emulsifier exhibited low fluid loss at about 325° F. (about 162.8° C.) and a low amount of water in the filtrate. The drilling fluid including the emulsifier appeared to be stable, but exhibited a small amount of water in the filtrate during the HPHT fluid loss testing. The amount of the water in the filtrate may be reduced by providing a wetting agent, increasing the amount of the emulsifier in the composition, and/or providing an additional emulsifier in the composition.

The embodiments of wellbore (e.g., drilling) fluids including the emulsifiers have been primarily described with reference to wellbore drilling operations; the emulsifiers described herein may be used in applications other than the drilling of a wellbore. In other embodiments, completion fluids and injected fluids including the emulsifiers according to the present disclosure may be used outside a wellbore or other downhole environment used for the exploration or production of natural resources. Accordingly, the terms "wellbore," "borehole," and the like should not be interpreted to limit tools, systems, assemblies, or methods of the present disclosure to any particular industry, field, or environment. In addition, the wellbore fluids may be used in cased completion wellbores and in open hole completion wellbores.

In some embodiments, the wellbore fluids may be used during formation of a wellbore to be used for carbon capture, utilization, and storage (CCUS) and/or for recovery and use of geothermal energy. Geothermal energy is a promising source of renewable energy that captures energy from heat generated within the earth. For example, geothermal energy may be used to heat structures (e.g., buildings) and/or to generate electricity (e.g., by heating water to generate steam and drive a turbine with the steam). The wellbore fluids including the emulsifiers described herein may be used to form wellbores used to circulate a fluid that is heated within the earth formation through which the wellbore extends. The heated fluid may be circulated to the surface where the captured heat may be recovered to heat a structure and/or generate electricity, followed by recirculation of the fluid to the earth formation to continue the cycle.

CCUS facilitates the capture, use, and/or storage of carbon (e.g., carbon dioxide), which has a goal of achieving carbon neutrality and/or net zero carbon emissions (NZE). CCUS may facilitate the capture of carbon dioxide from large point sources (e.g., power plants, refineries, cement plants, other industrial processing plants, or other industrial facilities that use fossil fuels, biomass fuels, or other fuels that generate carbon dioxide). The captured carbon dioxide may be converted into valuable products such as, for example, ethanol, sustainable aviation fuel, chemicals, and mineral aggregates. Alternatively, the carbon dioxide may be stored in geologic formations, such as in depleted hydrocarbon reservoirs. The carbon dioxide may be introduced into the earth formation through a wellbore formed using the wellbore fluids described herein. In the earth formation, the carbon dioxide may be dispersed in an aqueous phase and stored as carbon dioxide, in mineral form (e.g., as a carbonate, such as calcium carbonate, magnesium carbonate, iron (II) carbonate), or as another form of carbon. The wellbore fluids including the emulsifiers described herein may be used to form wellbores for CCUS, such as for carbon storage.

One or more specific embodiments of the present disclosure are described herein. These described embodiments are examples of the presently disclosed techniques. Additionally, in an effort to provide a concise description of these embodiments, not all features of an actual embodiment may be described in the specification. It should be appreciated that in the development of any such actual implementation, as in any engineering or design project, numerous embodiment-specific decisions will be made to achieve the developers' specific goals, such as compliance with system-related and business-related constraints, which may vary from one embodiment to another. Moreover, it should be appreciated that such a development effort might be complex and time consuming, but would nevertheless be a routine undertaking of design, fabrication, and manufacture for those of ordinary skill having the benefit of this disclosure.

The articles "a," "an," and "the" are intended to mean that there are one or more of the elements in the preceding descriptions. The terms "comprising," "including," and "having" are intended to be inclusive and mean that there may be additional elements other than the listed elements.

Additionally, it should be understood that references to "one embodiment" or "an embodiment" of the present disclosure are not intended to be interpreted as excluding the existence of additional embodiments that also incorporate the recited features. For example, any element described in relation to an embodiment herein may be combinable with any element of any other embodiment described herein. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

The present disclosure may be embodied in other specific forms without departing from its spirit or characteristics. The described embodiments are to be considered as illustrative and not restrictive. The scope of the disclosure is, therefore, indicated by the appended claims rather than by the foregoing description. Changes that come within the meaning and range of equivalency of the claims are to be embraced within their scope.

What is claimed is:

1. A wellbore fluid, comprising:
an oleaginous base fluid; and
an emulsifier including a reaction product of:
a bis-amide and a sultone; and
an imidazoline-amide and the sultone,
wherein the emulsifier includes a weight ratio of the reaction product of the bis-amide and the sultone to the reaction product of the imidazoline-amide and the sultone within a range of from about 0.1:1.0 to about 1.0:10.0.

2. The wellbore fluid of claim 1, wherein the sultone includes 1,3-propane sultone.

3. The wellbore fluid of claim 1, wherein the sultone includes 1,4-butane sultone.

4. The wellbore fluid of claim 1, wherein the emulsifier includes the following structure:

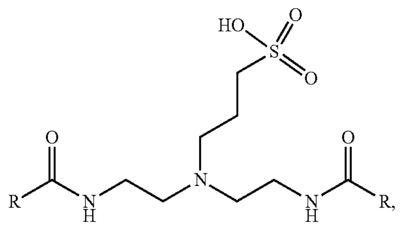

wherein R is a fatty acid without a hydroxyl group.

5. The wellbore fluid of claim 1, wherein the emulsifier includes the following structure:

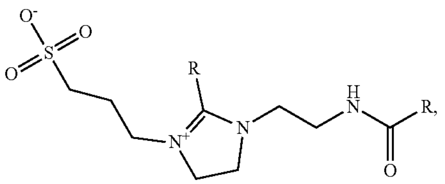

wherein R is a fatty acid without a hydroxyl group.

6. The wellbore fluid of claim 1, wherein the bis-amide and the imidazoline-amide include a reaction product of a polyalkylamine and a fatty acid.

7. The wellbore fluid of claim 1, wherein the bis-amide and the imidazoline-amide include a reaction product of diethylenetriamine and a fatty acid.

8. The wellbore fluid of claim 7, wherein the fatty acid includes one or more of oleic acid, linoleic acid, palmitic acid, and stearic acid.

9. A method of drilling a borehole, the method comprising:
drilling a borehole in an earth formation using a drilling fluid comprising:
an oleaginous base fluid; and
an emulsifier including a reaction product of:
a bis-amide and a sultone; and
an imidazoline-amide and the sultone; and
circulating the drilling fluid through the borehole,
wherein the emulsifier includes a weight ratio of the reaction product of the bis-amide and the sultone to the reaction product of the imidazoline-amide and the sultone within a range of from about 0.1:1.0 to about 1.0:10.0.

10. The method of claim 9, wherein the sultone includes 1,3-propane sultone.

11. The method of claim 9, wherein the sultone includes 1,4-butane sultone.

* * * * *